(12) United States Patent
Tajima et al.

(10) Patent No.: US 8,367,371 B2
(45) Date of Patent: Feb. 5, 2013

(54) METHOD FOR PRODUCTION OF L-AMINO ACID

(75) Inventors: Yoshinori Tajima, Kawasaki (JP); Shintaro Iwatani, Kawasaki (JP); Yoshihiro Usuda, Kawasaki (JP); Kazuhiko Matsui, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 344 days.

(21) Appl. No.: 12/420,934

(22) Filed: Apr. 9, 2009

(65) Prior Publication Data

US 2009/0239269 A1  Sep. 24, 2009

Related U.S. Application Data

(63) Continuation of application No. PCT/JP2007/068386, filed on Sep. 21, 2007.

(30) Foreign Application Priority Data

Oct. 10, 2006  (JP) .................................. 2006-276657

(51) Int. Cl.
*C12P 1/00* (2006.01)

(52) U.S. Cl. ........................................................ 435/41

(58) Field of Classification Search ........................ None
See application file for complete search history.

(56) References Cited

U.S. PATENT DOCUMENTS

| | | | |
|---|---|---|---|
| 5,168,056 A | 12/1992 | Frost | |
| 5,175,107 A | 12/1992 | Debabov et al. | |
| 5,618,716 A | 4/1997 | Burlingame | |
| 5,661,012 A | 8/1997 | Sano et al. | |
| 5,688,671 A | 11/1997 | Sugimoto et al. | |
| 5,776,736 A | 7/1998 | Frost et al. | |
| 5,827,698 A | 10/1998 | Kikuchi et al. | |
| 5,830,716 A | 11/1998 | Kojima et al. | |
| 5,832,453 A | 11/1998 | O'Brien | |
| 5,856,148 A | 1/1999 | Burlingame | |
| 5,906,925 A | 5/1999 | Liao | |
| 5,932,453 A | 8/1999 | Kikuchi et al. | |
| 5,985,617 A | 11/1999 | Liao | |
| 6,040,160 A | 3/2000 | Kojima et al. | |
| 6,132,999 A | 10/2000 | Debabov et al. | |
| 6,180,373 B1 | 1/2001 | Wich et al. | |
| 6,303,348 B1 | 10/2001 | Livshits et al. | |
| 6,319,696 B1 | 11/2001 | Kishino et al. | |
| 6,489,100 B1 | 12/2002 | Liao | |
| 6,911,332 B2 | 6/2005 | Usuda et al. | |
| 6,960,455 B2 | 11/2005 | Livshits et al. | |
| 7,026,149 B2 | 4/2006 | Usuda et al. | |
| 7,029,893 B2 | 4/2006 | Usuda et al. | |
| 7,045,320 B2 | 5/2006 | Iwatani et al. | |
| 7,060,475 B2 | 6/2006 | Usuda et al. | |
| 7,090,998 B2 | 8/2006 | Ishikawa et al. | |
| 7,186,531 B2 | 3/2007 | Akhverdian et al. | |
| 7,192,748 B2 | 3/2007 | Usuda et al. | |
| 7,220,570 B2 | 5/2007 | Usuda et al. | |
| 7,300,776 B2 | 11/2007 | Ito et al. | |
| 7,306,933 B2 | 12/2007 | Dien et al. | |
| 7,468,262 B2 | 12/2008 | Usuda et al. | |
| 2002/0025564 A1 | 2/2002 | Kobayashi et al. | |
| 2002/0110876 A1 | 8/2002 | Miyata et al. | |
| 2002/0155556 A1 | 10/2002 | Imaizumi et al. | |
| 2002/0160461 A1 | 10/2002 | Nakai et al. | |
| 2003/0157667 A1 | 8/2003 | Vitushkina et al. | |
| 2004/0132165 A1 | 7/2004 | Akhverdian et al. | |
| 2004/0265956 A1 | 12/2004 | Takikawa et al. | |
| 2005/0103275 A1 | 5/2005 | Sasaki et al. | |
| 2005/0191684 A1 | 9/2005 | Zimenkov et al. | |
| 2005/0233308 A1 | 10/2005 | Nishio et al. | |
| 2005/0239177 A1 | 10/2005 | Livshits et al. | |
| 2006/0019355 A1 | 1/2006 | Ueda et al. | |
| 2006/0035348 A1 | 2/2006 | Gulevich et al. | |
| 2006/0088919 A1 | 4/2006 | Rybak et al. | |
| 2006/0216796 A1 | 9/2006 | Hashiguchi et al. | |
| 2006/0234356 A1 | 10/2006 | Usuda et al. | |
| 2006/0234357 A1 | 10/2006 | Usuda et al. | |
| 2007/0004014 A1 | 1/2007 | Tsuji et al. | |
| 2007/0249017 A1 | 10/2007 | Usuda et al. | |
| 2009/0068712 A1 | 3/2009 | Terashita et al. | |
| 2009/0093029 A1 | 4/2009 | Usuda et al. | |

FOREIGN PATENT DOCUMENTS

| | | |
|---|---|---|
| EP | 1 270 721 | 1/2003 |
| JP | 2000-236893 | 9/2000 |
| RU | 2264457 | 11/2005 |
| WO | WO95/33843 | 12/1995 |
| WO | WO01/53459 | 7/2001 |
| WO | WO2005/103275 | 11/2005 |
| WO | WO2006/038695 | 4/2006 |
| WO | WO2007/037503 | 4/2007 |
| WO | 2007068386 | * 9/2007 |

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Ma et al, GadE (YhiE) activates glutamate decarboxylase-dependent acid resistance in *Escherichia coli* K-12. Mol Microbiol. Sep. 2003;49(5):1309-20.*
De Biase et al, Isolation, Overexpression, and Biochemical Characterization of the Two Isoforms of Glutamic Acid Decarboxylase from*Escherichia coli* Protein Expr Purif. Dec. 1996;8(4):430-8.*
Supplementary European Search Report for EP Patent App. No. 07828306.6 (Nov. 20, 2009).
International Search Report for PCT Patent App. No. PCT/JP2007/068386 (Oct. 16, 2007).
Castanie-Cornett, M.-P., et al., "Control of Acid Resistance in *Escherichia coli*," J. Bacteriol. 1990;181(11):3525-3535.

(Continued)

*Primary Examiner* — Sheridan Swope

(74) *Attorney, Agent, or Firm* — Shelly Guest Cermak; Cermak Nakajima LLP

(57) ABSTRACT

A bacterium which belongs to the Enterobacteriaceae family and has an ability to produce an L-amino acid such as L-lysine, L-threonine and L-tryptophan and is modified to enhance glutamic acid decarboxylase activity is cultured in a medium to produce and accumulate the L-amino acid in the medium or cells of the bacterium. Then, the L-amino acid is collected from the medium or the cells.

2 Claims, No Drawings

OTHER PUBLICATIONS

Fonda, M. L., "L-Glutamate Decarboxylase from Bacteria," Methods in Enzymology 1985;113:11-16.

Hersh, B. M., et al., "A Glutamate-Dependent Acid Resistance Gene in *Escherichia coli*," J. Bacteriol. 1996;178(13):3978-3981.

Ma, Z., et al., "Characterization of EvgAS-YdeO-GadE Branched Regulatory Circuit Governing Glutamate-Dependent Acid Resistance in *Escherichia coli*," J. Bacteriol. 2004;186(21):7378-7389.

Smith, D. K., et al., "*Escherichia coli* Has Two Homologous Glutamate Decarboxylase Genes That Map to Distinct Loci," J. Bacteriol. 1992;174(18):5820-5826.

International Preliminary Report on Patentability for PCT Patent App. No. PCT/JP2007/068386 (Apr. 30, 2009).

Castanie-Cornet, M.-P., et al., "Control of Acid Resistance in *Escherichia coli*," J. Bacteriol. 1999;181(11):3525-3535.

\* cited by examiner

SEQUENCE LISTING

```
<160> NUMBER OF SEQ ID NOS: 25

<210> SEQ ID NO 1
<211> LENGTH: 1401
<212> TYPE: DNA
<213> ORGANISM: Escherichia coli
<220> FEATURE:
<221> NAME/KEY: CDS
<222> LOCATION: (1)..(1398)

<400> SEQUENCE: 1 atg gac cag aag ctg tta acg gat ttc cgc tca gaa cta ctc gat tca        48
Met Asp Gln Lys Leu Leu Thr Asp Phe Arg Ser Glu Leu Leu Asp Ser
1               5                   10                  15 cgt ttt ggc gca aag gcc att tct act atc gcg gag tca aaa cga ttt        96
Arg Phe Gly Ala Lys Ala Ile Ser Thr Ile Ala Glu Ser Lys Arg Phe
            20                  25                  30 ccg ctg cac gaa atg cgc gat gat gtc gca ttt cag att atc aat gat       144
Pro Leu His Glu Met Arg Asp Asp Val Ala Phe Gln Ile Ile Asn Asp
        35                  40                  45 gaa tta tat ctt gat ggc aac gct cgt cag aac ctg gcc act ttc tgc       192
```

```
                Glu Leu Tyr Leu Asp Gly Asn Ala Arg Gln Asn Leu Ala Thr Phe Cys
                     50                  55                  60 cag acc tgg gac gac gaa aac gtc cat aaa ttg atg gat ttg tcg atc                  240
Gln Thr Trp Asp Asp Glu Asn Val His Lys Leu Met Asp Leu Ser Ile
 65                  70                  75                  80 aat aaa aac tgg atc gac aaa gaa gaa tat ccg caa tcc gca gcc atc                  288
Asn Lys Asn Trp Ile Asp Lys Glu Glu Tyr Pro Gln Ser Ala Ala Ile
                 85                  90                  95 gac ctg cgt tgc gta aat atg gtt gcc gat ctg tgg cat gcg cct gcg                  336
Asp Leu Arg Cys Val Asn Met Val Ala Asp Leu Trp His Ala Pro Ala
             100                 105                 110 ccg aaa aat ggt cag gcc gtt ggc acc aac acc att ggt tct tcc gag                  384
Pro Lys Asn Gly Gln Ala Val Gly Thr Asn Thr Ile Gly Ser Ser Glu
             115                 120                 125 gcc tgt atg ctc ggc ggg atg gcg atg aaa tgg cgt tgg cgc aag cgt                  432
Ala Cys Met Leu Gly Gly Met Ala Met Lys Trp Arg Trp Arg Lys Arg
         130                 135                 140 atg gaa gct gca ggc aaa cca acg gat aaa cca aac ctg gtg tgc ggt                  480
Met Glu Ala Ala Gly Lys Pro Thr Asp Lys Pro Asn Leu Val Cys Gly
145                 150                 155                 160 ccg gta caa atc tgc tgg cat aaa ttc gcc cgc tac tgg gat gtg gag                  528
Pro Val Gln Ile Cys Trp His Lys Phe Ala Arg Tyr Trp Asp Val Glu
                165                 170                 175 ctg cgt gag atc cct atg cgc ccc ggt cag ttg ttt atg gac ccg aaa                  576
Leu Arg Glu Ile Pro Met Arg Pro Gly Gln Leu Phe Met Asp Pro Lys
            180                 185                 190 cgc atg att gaa gcc tgt gac gaa aac acc atc ggc gtg gtg ccg act                  624
Arg Met Ile Glu Ala Cys Asp Glu Asn Thr Ile Gly Val Val Pro Thr
            195                 200                 205 ttc ggc gtg acc tac acc ggt aac tat gag ttc cca caa ccg ctg cac                  672
Phe Gly Val Thr Tyr Thr Gly Asn Tyr Glu Phe Pro Gln Pro Leu His
        210                 215                 220 gat gcg ctg gat aaa ttc cag gcc gac acc ggt atc gac atc gac atg                  720
Asp Ala Leu Asp Lys Phe Gln Ala Asp Thr Gly Ile Asp Ile Asp Met
225                 230                 235                 240 cac atc gac gct gcc agc ggt ggc ttc ctg gca ccg ttc gtc gcc ccg                  768
His Ile Asp Ala Ala Ser Gly Gly Phe Leu Ala Pro Phe Val Ala Pro
                245                 250                 255 gat atc gtc tgg gac ttc cgc ctg ccg cgt gtg aaa tcg atc agt gct                  816
Asp Ile Val Trp Asp Phe Arg Leu Pro Arg Val Lys Ser Ile Ser Ala
            260                 265                 270 tca ggc cat aaa ttc ggt ctg gct ccg ctg ggc tgc ggc tgg gtt atc                  864
Ser Gly His Lys Phe Gly Leu Ala Pro Leu Gly Cys Gly Trp Val Ile
            275                 280                 285 tgg cgt gac gaa gaa gcg ctg ccg cag gaa ctg gtg ttc aac gtt gac                  912
Trp Arg Asp Glu Glu Ala Leu Pro Gln Glu Leu Val Phe Asn Val Asp
        290                 295                 300 tac ctg ggt ggt caa att ggt act ttt gcc atc aac ttc tcc cgc ccg                  960
Tyr Leu Gly Gly Gln Ile Gly Thr Phe Ala Ile Asn Phe Ser Arg Pro
305                 310                 315                 320 gcg ggt cag gta att gca cag tac tat gaa ttc ctg cgc ctc ggt cgt                 1008
Ala Gly Gln Val Ile Ala Gln Tyr Tyr Glu Phe Leu Arg Leu Gly Arg
                325                 330                 335 gaa ggc tat acc aaa gta cag aac gcc tct tac cag gtt gcc gct tat                 1056
Glu Gly Tyr Thr Lys Val Gln Asn Ala Ser Tyr Gln Val Ala Ala Tyr
            340                 345                 350 ctg gcg gat gaa atc gcc aaa ctg ggg ccg tat gag ttc atc tgt acg                 1104
Leu Ala Asp Glu Ile Ala Lys Leu Gly Pro Tyr Glu Phe Ile Cys Thr
            355                 360                 365 ggt cgc ccg gac gaa ggc atc ccg gcg gtt tgc ttc aaa ctg aaa gat                 1152
```

```
Gly Arg Pro Asp Glu Gly Ile Pro Ala Val Cys Phe Lys Leu Lys Asp
        370                 375                 380 ggt gaa gat ccg gga tac acc ctg tac gac ctc tct gaa cgt ctg cgt         1200
Gly Glu Asp Pro Gly Tyr Thr Leu Tyr Asp Leu Ser Glu Arg Leu Arg
385                 390                 395                 400 ctg cgc ggc tgg cag gtt ccg gcc ttc act ctc ggc ggt gaa gcc acc         1248
Leu Arg Gly Trp Gln Val Pro Ala Phe Thr Leu Gly Gly Glu Ala Thr
                405                 410                 415 gac atc gtg gtg atg cgc att atg tgt cgt cgc ggc ttc gaa atg gac         1296
Asp Ile Val Val Met Arg Ile Met Cys Arg Arg Gly Phe Glu Met Asp
            420                 425                 430 ttt gct gaa ctg ttg ctg gaa gac tac aaa gcc tcc ctg aaa tat ctc         1344
Phe Ala Glu Leu Leu Leu Glu Asp Tyr Lys Ala Ser Leu Lys Tyr Leu
        435                 440                 445 agc gat cac ccg aaa ctg cag ggt att gcc cag cag aac agc ttt aaa         1392
Ser Asp His Pro Lys Leu Gln Gly Ile Ala Gln Gln Asn Ser Phe Lys
    450                 455                 460 cac acc tga                                                             1401
His Thr
465

<210> SEQ ID NO 2
<211> LENGTH: 466
<212> TYPE: PRT
<213> ORGANISM: Escherichia coli

<400> SEQUENCE: 2

Met Asp Gln Lys Leu Leu Thr Asp Phe Arg Ser Glu Leu Leu Asp Ser
1               5                   10                  15

Arg Phe Gly Ala Lys Ala Ile Ser Thr Ile Ala Glu Ser Lys Arg Phe
            20                  25                  30

Pro Leu His Glu Met Arg Asp Asp Val Ala Phe Gln Ile Ile Asn Asp
        35                  40                  45

Glu Leu Tyr Leu Asp Gly Asn Ala Arg Gln Asn Leu Ala Thr Phe Cys
    50                  55                  60

Gln Thr Trp Asp Asp Glu Asn Val His Lys Leu Met Asp Leu Ser Ile
65                  70                  75                  80

Asn Lys Asn Trp Ile Asp Lys Glu Glu Tyr Pro Gln Ser Ala Ala Ile
                85                  90                  95

Asp Leu Arg Cys Val Asn Met Val Ala Asp Leu Trp His Ala Pro Ala
            100                 105                 110

Pro Lys Asn Gly Gln Ala Val Gly Thr Asn Thr Ile Gly Ser Ser Glu
        115                 120                 125

Ala Cys Met Leu Gly Gly Met Ala Met Lys Trp Arg Trp Arg Lys Arg
    130                 135                 140

Met Glu Ala Ala Gly Lys Pro Thr Asp Lys Pro Asn Leu Val Cys Gly
145                 150                 155                 160

Pro Val Gln Ile Cys Trp His Lys Phe Ala Arg Tyr Trp Asp Val Glu
                165                 170                 175

Leu Arg Glu Ile Pro Met Arg Pro Gly Gln Leu Phe Met Asp Pro Lys
            180                 185                 190

Arg Met Ile Glu Ala Cys Asp Glu Asn Thr Ile Gly Val Val Pro Thr
        195                 200                 205

Phe Gly Val Thr Tyr Thr Gly Asn Tyr Glu Phe Pro Gln Pro Leu His
    210                 215                 220

Asp Ala Leu Asp Lys Phe Gln Ala Asp Thr Gly Ile Asp Ile Asp Met
225                 230                 235                 240
```

-continued

```
His Ile Asp Ala Ala Ser Gly Gly Phe Leu Ala Pro Phe Val Ala Pro
                245                 250                 255

Asp Ile Val Trp Asp Phe Arg Leu Pro Arg Val Lys Ser Ile Ser Ala
            260                 265                 270

Ser Gly His Lys Phe Gly Leu Ala Pro Leu Gly Cys Gly Trp Val Ile
        275                 280                 285

Trp Arg Asp Glu Glu Ala Leu Pro Gln Glu Leu Val Phe Asn Val Asp
    290                 295                 300

Tyr Leu Gly Gly Gln Ile Gly Thr Phe Ala Ile Asn Phe Ser Arg Pro
305                 310                 315                 320

Ala Gly Gln Val Ile Ala Gln Tyr Tyr Glu Phe Leu Arg Leu Gly Arg
                325                 330                 335

Glu Gly Tyr Thr Lys Val Gln Asn Ala Ser Tyr Gln Val Ala Ala Tyr
            340                 345                 350

Leu Ala Asp Glu Ile Ala Lys Leu Gly Pro Tyr Glu Phe Ile Cys Thr
        355                 360                 365

Gly Arg Pro Asp Glu Gly Ile Pro Ala Val Cys Phe Lys Leu Lys Asp
    370                 375                 380

Gly Glu Asp Pro Gly Tyr Thr Leu Tyr Asp Leu Ser Glu Arg Leu Arg
385                 390                 395                 400

Leu Arg Gly Trp Gln Val Pro Ala Phe Thr Leu Gly Gly Glu Ala Thr
                405                 410                 415

Asp Ile Val Val Met Arg Ile Met Cys Arg Arg Gly Phe Glu Met Asp
            420                 425                 430

Phe Ala Glu Leu Leu Leu Glu Asp Tyr Lys Ala Ser Leu Lys Tyr Leu
        435                 440                 445

Ser Asp His Pro Lys Leu Gln Gly Ile Ala Gln Gln Asn Ser Phe Lys
    450                 455                 460

His Thr
465

<210> SEQ ID NO 3
<211> LENGTH: 1401
<212> TYPE: DNA
<213> ORGANISM: Escherichia coli
<220> FEATURE:
<221> NAME/KEY: CDS
<222> LOCATION: (1)..(1398)

<400> SEQUENCE: 3 atg gat aag aag caa gta acg gat tta agg tcg gaa cta ctc gat tca      48
Met Asp Lys Lys Gln Val Thr Asp Leu Arg Ser Glu Leu Leu Asp Ser
1               5                   10                  15 cgt ttt ggt gcg aag tct att tcc act atc gca gaa tca aaa cgt ttt      96
Arg Phe Gly Ala Lys Ser Ile Ser Thr Ile Ala Glu Ser Lys Arg Phe
            20                  25                  30 ccg ctg cac gaa atg cgc gac gat gtc gca ttc cag att atc aat gac     144
Pro Leu His Glu Met Arg Asp Asp Val Ala Phe Gln Ile Ile Asn Asp
        35                  40                  45 gaa tta tat ctt gat ggc aac gct cgt cag aac ctg gcc act ttc tgc     192
Glu Leu Tyr Leu Asp Gly Asn Ala Arg Gln Asn Leu Ala Thr Phe Cys
    50                  55                  60 cag acc tgg gac gac gaa aat gtc cac aaa ttg atg gat tta tcc att     240
Gln Thr Trp Asp Asp Glu Asn Val His Lys Leu Met Asp Leu Ser Ile
65                  70                  75                  80 aac aaa aac tgg atc gac aaa gaa gaa tat ccg caa tcc gca gcc atc     288
Asn Lys Asn Trp Ile Asp Lys Glu Glu Tyr Pro Gln Ser Ala Ala Ile
                85                  90                  95
```

```
gac ctg cgt tgc gta aat atg gtt gcc gat ctg tgg cat gcg cct gcg      336
Asp Leu Arg Cys Val Asn Met Val Ala Asp Leu Trp His Ala Pro Ala
        100                 105                 110 ccg aaa aat ggt cag gcc gtt ggc acc aac acc att ggt tct tcc gag      384
Pro Lys Asn Gly Gln Ala Val Gly Thr Asn Thr Ile Gly Ser Ser Glu
        115                 120                 125 gcc tgt atg ctc ggc ggg atg gcg atg aaa tgg cgt tgg cgc aag cgt      432
Ala Cys Met Leu Gly Gly Met Ala Met Lys Trp Arg Trp Arg Lys Arg
130                 135                 140 atg gaa gct gca ggc aaa cca acg gat aaa cca aac ctg gtg tgc ggt      480
Met Glu Ala Ala Gly Lys Pro Thr Asp Lys Pro Asn Leu Val Cys Gly
145                 150                 155                 160 ccg gta caa atc tgc tgg cat aaa ttc gcc cgc tac tgg gat gtg gag      528
Pro Val Gln Ile Cys Trp His Lys Phe Ala Arg Tyr Trp Asp Val Glu
                165                 170                 175 ctg cgt gag atc cct atg cgc ccc ggt cag ttg ttt atg gac ccg aaa      576
Leu Arg Glu Ile Pro Met Arg Pro Gly Gln Leu Phe Met Asp Pro Lys
                180                 185                 190 cgc atg att gaa gcc tgt gac gaa aac acc atc ggc gtg gtg ccg act      624
Arg Met Ile Glu Ala Cys Asp Glu Asn Thr Ile Gly Val Val Pro Thr
            195                 200                 205 ttc ggc gtg acc tac act ggt aac tat gag ttc cca caa ccg ctg cac      672
Phe Gly Val Thr Tyr Thr Gly Asn Tyr Glu Phe Pro Gln Pro Leu His
210                 215                 220 gat gcg ctg gat aaa ttc cag gcc gat acc ggt atc gac atc gac atg      720
Asp Ala Leu Asp Lys Phe Gln Ala Asp Thr Gly Ile Asp Ile Asp Met
225                 230                 235                 240 cac atc gac gct gcc agc ggt ggc ttc ctg gca ccg ttc gtc gcc ccg      768
His Ile Asp Ala Ala Ser Gly Gly Phe Leu Ala Pro Phe Val Ala Pro
                245                 250                 255 gat atc gtc tgg gac ttc cgc ctg ccg cgt gtg aaa tcg atc agt gct      816
Asp Ile Val Trp Asp Phe Arg Leu Pro Arg Val Lys Ser Ile Ser Ala
                260                 265                 270 tca ggc cat aaa ttc ggt ctg gct ccg ctg ggc tgc ggc tgg gtt atc      864
Ser Gly His Lys Phe Gly Leu Ala Pro Leu Gly Cys Gly Trp Val Ile
            275                 280                 285 tgg cgt gac gaa gaa gcg ctg ccg cag gaa ctg gtg ttc aac gtt gac      912
Trp Arg Asp Glu Glu Ala Leu Pro Gln Glu Leu Val Phe Asn Val Asp
290                 295                 300 tac ctg ggt ggt caa att ggt act ttt gcc atc aac ttc tcc cgc ccg      960
Tyr Leu Gly Gly Gln Ile Gly Thr Phe Ala Ile Asn Phe Ser Arg Pro
305                 310                 315                 320 gcg ggt cag gta att gca cag tac tat gaa ttc ctg cgc ctc ggt cgt     1008
Ala Gly Gln Val Ile Ala Gln Tyr Tyr Glu Phe Leu Arg Leu Gly Arg
                325                 330                 335 gaa ggc tat acc aaa gta cag aac gcc tct tac cag gtt gcc gct tat     1056
Glu Gly Tyr Thr Lys Val Gln Asn Ala Ser Tyr Gln Val Ala Ala Tyr
            340                 345                 350 ctg gcg gat gaa atc gcc aaa ctg ggg ccg tat gag ttc atc tgt acg     1104
Leu Ala Asp Glu Ile Ala Lys Leu Gly Pro Tyr Glu Phe Ile Cys Thr
                355                 360                 365 ggt cgc ccg gac gaa ggc atc ccg gcg gtt tgc ttc aaa ctg aaa gat     1152
Gly Arg Pro Asp Glu Gly Ile Pro Ala Val Cys Phe Lys Leu Lys Asp
370                 375                 380 ggt gaa gat ccg gga tac acc ctg tat gac ctc tct gaa cgt ctg cgt     1200
Gly Glu Asp Pro Gly Tyr Thr Leu Tyr Asp Leu Ser Glu Arg Leu Arg
385                 390                 395                 400 ctg cgc ggc tgg cag gtt ccg gcc ttc act ctc ggc ggt gaa gcc acc     1248
Leu Arg Gly Trp Gln Val Pro Ala Phe Thr Leu Gly Gly Glu Ala Thr
                405                 410                 415
```

```
gac atc gtg gtg atg cgc att atg tgt cgt cgc ggc ttc gaa atg gac      1296
Asp Ile Val Val Met Arg Ile Met Cys Arg Arg Gly Phe Glu Met Asp
        420                 425                 430 ttt gct gaa ctg ttg ctg gaa gac tac aaa gcc tcc ctg aaa tat ctc      1344
Phe Ala Glu Leu Leu Leu Glu Asp Tyr Lys Ala Ser Leu Lys Tyr Leu
            435                 440                 445 agc gat cac ccg aaa ctg cag ggt att gcc caa cag aac agc ttt aaa      1392
Ser Asp His Pro Lys Leu Gln Gly Ile Ala Gln Gln Asn Ser Phe Lys
450                 455                 460 cat acc tga                                                          1401
His Thr
465

<210> SEQ ID NO 4
<211> LENGTH: 466
<212> TYPE: PRT
<213> ORGANISM: Escherichia coli

<400> SEQUENCE: 4

Met Asp Lys Lys Gln Val Thr Asp Leu Arg Ser Glu Leu Leu Asp Ser
1               5                   10                  15

Arg Phe Gly Ala Lys Ser Ile Ser Thr Ile Ala Glu Ser Lys Arg Phe
            20                  25                  30

Pro Leu His Glu Met Arg Asp Asp Val Ala Phe Gln Ile Ile Asn Asp
        35                  40                  45

Glu Leu Tyr Leu Asp Gly Asn Ala Arg Gln Asn Leu Ala Thr Phe Cys
    50                  55                  60

Gln Thr Trp Asp Asp Glu Asn Val His Lys Leu Met Asp Leu Ser Ile
65                  70                  75                  80

Asn Lys Asn Trp Ile Asp Lys Glu Glu Tyr Pro Gln Ser Ala Ala Ile
                85                  90                  95

Asp Leu Arg Cys Val Asn Met Val Ala Asp Leu Trp His Ala Pro Ala
            100                 105                 110

Pro Lys Asn Gly Gln Ala Val Gly Thr Asn Thr Ile Gly Ser Ser Glu
        115                 120                 125

Ala Cys Met Leu Gly Gly Met Ala Met Lys Trp Arg Trp Arg Lys Arg
    130                 135                 140

Met Glu Ala Ala Gly Lys Pro Thr Asp Lys Pro Asn Leu Val Cys Gly
145                 150                 155                 160

Pro Val Gln Ile Cys Trp His Lys Phe Ala Arg Tyr Trp Asp Val Glu
                165                 170                 175

Leu Arg Glu Ile Pro Met Arg Pro Gly Gln Leu Phe Met Asp Pro Lys
            180                 185                 190

Arg Met Ile Glu Ala Cys Asp Glu Asn Thr Ile Gly Val Val Pro Thr
        195                 200                 205

Phe Gly Val Thr Tyr Thr Gly Asn Tyr Glu Phe Pro Gln Pro Leu His
    210                 215                 220

Asp Ala Leu Asp Lys Phe Gln Ala Asp Thr Gly Ile Asp Ile Asp Met
225                 230                 235                 240

His Ile Asp Ala Ala Ser Gly Gly Phe Leu Ala Pro Phe Val Ala Pro
                245                 250                 255

Asp Ile Val Trp Asp Phe Arg Leu Pro Arg Val Lys Ser Ile Ser Ala
            260                 265                 270

Ser Gly His Lys Phe Gly Leu Ala Pro Leu Gly Cys Gly Trp Val Ile
        275                 280                 285

Trp Arg Asp Glu Glu Ala Leu Pro Gln Glu Leu Val Phe Asn Val Asp
    290                 295                 300
```

```
Tyr Leu Gly Gly Gln Ile Gly Thr Phe Ala Ile Asn Phe Ser Arg Pro
305                 310                 315                 320

Ala Gly Gln Val Ile Ala Gln Tyr Tyr Glu Phe Leu Arg Leu Gly Arg
                325                 330                 335

Glu Gly Tyr Thr Lys Val Gln Asn Ala Ser Tyr Gln Val Ala Ala Tyr
            340                 345                 350

Leu Ala Asp Glu Ile Ala Lys Leu Gly Pro Tyr Glu Phe Ile Cys Thr
        355                 360                 365

Gly Arg Pro Asp Glu Gly Ile Pro Ala Val Cys Phe Lys Leu Lys Asp
    370                 375                 380

Gly Glu Asp Pro Gly Tyr Thr Leu Tyr Asp Leu Ser Glu Arg Leu Arg
385                 390                 395                 400

Leu Arg Gly Trp Gln Val Pro Ala Phe Thr Leu Gly Gly Glu Ala Thr
                405                 410                 415

Asp Ile Val Val Met Arg Ile Met Cys Arg Arg Gly Phe Glu Met Asp
            420                 425                 430

Phe Ala Glu Leu Leu Leu Glu Asp Tyr Lys Ala Ser Leu Lys Tyr Leu
        435                 440                 445

Ser Asp His Pro Lys Leu Gln Gly Ile Ala Gln Gln Asn Ser Phe Lys
    450                 455                 460

His Thr
465

<210> SEQ ID NO 5
<211> LENGTH: 1536
<212> TYPE: DNA
<213> ORGANISM: Escherichia coli
<220> FEATURE:
<221> NAME/KEY: CDS
<222> LOCATION: (1)..(1533)

<400> SEQUENCE: 5 atg gct aca tca gta cag aca ggt aaa gct aag cag ctc aca tta ctt       48
Met Ala Thr Ser Val Gln Thr Gly Lys Ala Lys Gln Leu Thr Leu Leu
1               5                   10                  15 gga ttc ttt gcc ata acg gca tcg atg gta atg gct gtt tat gaa tac       96
Gly Phe Phe Ala Ile Thr Ala Ser Met Val Met Ala Val Tyr Glu Tyr
            20                  25                  30 cct acc ttc gca aca tcg ggc ttt tca tta gtc ttc ttc ctg cta tta      144
Pro Thr Phe Ala Thr Ser Gly Phe Ser Leu Val Phe Phe Leu Leu Leu
        35                  40                  45 ggc ggg att tta tgg ttt att ccc gtg gga ctt tgt gct gcg gaa atg      192
Gly Gly Ile Leu Trp Phe Ile Pro Val Gly Leu Cys Ala Ala Glu Met
    50                  55                  60 gcc acc gtc gac ggc tgg gaa gaa ggt ggt gtc ttc gcc tgg gta tca      240
Ala Thr Val Asp Gly Trp Glu Glu Gly Gly Val Phe Ala Trp Val Ser
65                  70                  75                  80 aat act ctg ggg ccg aga tgg gga ttt gca gcg atc tca ttt ggc tat      288
Asn Thr Leu Gly Pro Arg Trp Gly Phe Ala Ala Ile Ser Phe Gly Tyr
                85                  90                  95 ctg caa atc gcc att ggt ttt att ccg atg ctc tat ttc gtg tta ggg      336
Leu Gln Ile Ala Ile Gly Phe Ile Pro Met Leu Tyr Phe Val Leu Gly
            100                 105                 110 gca ctc tcc tac atc ctg aaa tgg cca gcg ctg aat gaa gac ccc att      384
Ala Leu Ser Tyr Ile Leu Lys Trp Pro Ala Leu Asn Glu Asp Pro Ile
        115                 120                 125 acc aaa act att gca gca ctc atc att ctt tgg gcg ctg gca tta acg      432
Thr Lys Thr Ile Ala Ala Leu Ile Ile Leu Trp Ala Leu Ala Leu Thr
    130                 135                 140
```

|  |  |
|---|---|
| cag ttt ggt ggc acg aaa tac acg gcg cga att gct aaa gtt ggc ttc<br>Gln Phe Gly Gly Thr Lys Tyr Thr Ala Arg Ile Ala Lys Val Gly Phe<br>145                    150                155                160 | 480 |
| ttc gcc ggt atc ctg tta cct gca ttt att ttg atc gca tta gcg gct<br>Phe Ala Gly Ile Leu Leu Pro Ala Phe Ile Leu Ile Ala Leu Ala Ala<br>                165                170                175 | 528 |
| att tat ctg cac tcc ggt gcc ccc gtt gct atc gaa atg gat tcg aag<br>Ile Tyr Leu His Ser Gly Ala Pro Val Ala Ile Glu Met Asp Ser Lys<br>           180                    185                190 | 576 |
| acc ttc ttc cct gac ttc tct aaa gtg ggc acc ctg gta gta ttt gtt<br>Thr Phe Phe Pro Asp Phe Ser Lys Val Gly Thr Leu Val Val Phe Val<br>                195                200                205 | 624 |
| gcc ttc att ttg agt tat atg ggc gta gaa gca tcc gca acc cac gtc<br>Ala Phe Ile Leu Ser Tyr Met Gly Val Glu Ala Ser Ala Thr His Val<br>      210                215                220 | 672 |
| aat gaa atg agc aac cca ggg cgc gac tat ccg ttg gct atg tta ctg<br>Asn Glu Met Ser Asn Pro Gly Arg Asp Tyr Pro Leu Ala Met Leu Leu<br>225                    230                235                240 | 720 |
| ctg atg gtg gcg gca atc tgc tta agc tct gtt ggt ggt ttg tct att<br>Leu Met Val Ala Ala Ile Cys Leu Ser Ser Val Gly Gly Leu Ser Ile<br>                245                250                255 | 768 |
| gcg atg gtc att ccg ggt aat gaa atc aac ctc tcc gca ggg gta atg<br>Ala Met Val Ile Pro Gly Asn Glu Ile Asn Leu Ser Ala Gly Val Met<br>           260                    265                270 | 816 |
| caa acc ttt acc gtt ctg atg tcc cat gtg gca cca gaa att gag tgg<br>Gln Thr Phe Thr Val Leu Met Ser His Val Ala Pro Glu Ile Glu Trp<br>                275                280                285 | 864 |
| acg gtt cgc gtg atc tcc gca ctg ctg ttg ctg ggt gtt ctg gcg gaa<br>Thr Val Arg Val Ile Ser Ala Leu Leu Leu Leu Gly Val Leu Ala Glu<br>      290              295                300 | 912 |
| atc gcc tcc tgg att gtt ggt cct tct cgc ggg atg tat gta aca gcg<br>Ile Ala Ser Trp Ile Val Gly Pro Ser Arg Gly Met Tyr Val Thr Ala<br>305                    310                315                320 | 960 |
| cag aaa aac ctg ctg cca gcg gca ttc gct aaa atg aac aaa aat ggc<br>Gln Lys Asn Leu Leu Pro Ala Ala Phe Ala Lys Met Asn Lys Asn Gly<br>                325                330                335 | 1008 |
| gta ccg gta acg ctg gtc att tcg cag ctg gtg att acg tct atc gcg<br>Val Pro Val Thr Leu Val Ile Ser Gln Leu Val Ile Thr Ser Ile Ala<br>           340                    345                350 | 1056 |
| ttg atc atc ctc acc aat acc ggt ggc ggt aac aac atg tcc ttc ctg<br>Leu Ile Ile Leu Thr Asn Thr Gly Gly Gly Asn Asn Met Ser Phe Leu<br>                355                360                365 | 1104 |
| atc gca ctg gcg ctg acg gtg gtg att tat ctg tgt gct tat ttc atg<br>Ile Ala Leu Ala Leu Thr Val Val Ile Tyr Leu Cys Ala Tyr Phe Met<br>      370              375                380 | 1152 |
| ctg ttt att ggc tac att gtg ttg gtt ctt aaa cat cct gac tta aaa<br>Leu Phe Ile Gly Tyr Ile Val Leu Val Leu Lys His Pro Asp Leu Lys<br>385                    390                395                400 | 1200 |
| cgc aca ttt aat atc cct ggt ggt aaa ggg gtg aaa ctg gtc gtg gca<br>Arg Thr Phe Asn Ile Pro Gly Gly Lys Gly Val Lys Leu Val Val Ala<br>                405                410                415 | 1248 |
| att gtc ggt ctg ctg act tca att atg gcg ttt att gtt tcc ttc ctg<br>Ile Val Gly Leu Leu Thr Ser Ile Met Ala Phe Ile Val Ser Phe Leu<br>           420                    425                430 | 1296 |
| ccg ccg gat aac atc cag ggt gat tct acc gat atg tat gtt gaa tta<br>Pro Pro Asp Asn Ile Gln Gly Asp Ser Thr Asp Met Tyr Val Glu Leu<br>                435                440                445 | 1344 |
| ctg gtt gtt agt ttc ctg gtg gta ctt gcc ctg ccc ttt att ctc tat<br>Leu Val Val Ser Phe Leu Val Val Leu Ala Leu Pro Phe Ile Leu Tyr<br>      450              455                460 | 1392 |

-continued

```
gct gtt cat gat cgt aaa ggc aaa gca aat acc ggc gtc act ctg gag      1440
Ala Val His Asp Arg Lys Gly Lys Ala Asn Thr Gly Val Thr Leu Glu
465                 470                 475                 480 cca atc aac agt cag aac gca cca aaa ggt cac ttc ttc ctg cac ccg      1488
Pro Ile Asn Ser Gln Asn Ala Pro Lys Gly His Phe Phe Leu His Pro
                485                 490                 495 cgt gca cgt tca cca cac tat att gtg atg aat gac aag aaa cac taa      1536
Arg Ala Arg Ser Pro His Tyr Ile Val Met Asn Asp Lys Lys His
            500                 505                 510
```

<210> SEQ ID NO 6
<211> LENGTH: 511
<212> TYPE: PRT
<213> ORGANISM: Escherichia coli

<400> SEQUENCE: 6

```
Met Ala Thr Ser Val Gln Thr Gly Lys Ala Lys Gln Leu Thr Leu Leu
1               5                   10                  15

Gly Phe Phe Ala Ile Thr Ala Ser Met Val Met Ala Val Tyr Glu Tyr
                20                  25                  30

Pro Thr Phe Ala Thr Ser Gly Phe Ser Leu Val Phe Phe Leu Leu Leu
            35                  40                  45

Gly Gly Ile Leu Trp Phe Ile Pro Val Gly Leu Cys Ala Ala Glu Met
        50                  55                  60

Ala Thr Val Asp Gly Trp Glu Glu Gly Val Phe Ala Trp Val Ser
65                  70                  75                  80

Asn Thr Leu Gly Pro Arg Trp Gly Phe Ala Ala Ile Ser Phe Gly Tyr
                85                  90                  95

Leu Gln Ile Ala Ile Gly Phe Ile Pro Met Leu Tyr Phe Val Leu Gly
            100                 105                 110

Ala Leu Ser Tyr Ile Leu Lys Trp Pro Ala Leu Asn Glu Asp Pro Ile
        115                 120                 125

Thr Lys Thr Ile Ala Ala Leu Ile Ile Leu Trp Ala Leu Ala Leu Thr
130                 135                 140

Gln Phe Gly Gly Thr Lys Tyr Thr Ala Arg Ile Ala Lys Val Gly Phe
145                 150                 155                 160

Phe Ala Gly Ile Leu Leu Pro Ala Phe Ile Leu Ile Ala Leu Ala Ala
                165                 170                 175

Ile Tyr Leu His Ser Gly Ala Pro Val Ala Ile Glu Met Asp Ser Lys
            180                 185                 190

Thr Phe Phe Pro Asp Phe Ser Lys Val Gly Thr Leu Val Val Phe Val
        195                 200                 205

Ala Phe Ile Leu Ser Tyr Met Gly Val Glu Ala Ser Ala Thr His Val
        210                 215                 220

Asn Glu Met Ser Asn Pro Gly Arg Asp Tyr Pro Leu Ala Met Leu Leu
225                 230                 235                 240

Leu Met Val Ala Ala Ile Cys Leu Ser Ser Val Gly Gly Leu Ser Ile
                245                 250                 255

Ala Met Val Ile Pro Gly Asn Glu Ile Asn Leu Ser Ala Gly Val Met
            260                 265                 270

Gln Thr Phe Thr Val Leu Met Ser His Val Ala Pro Glu Ile Glu Trp
        275                 280                 285

Thr Val Arg Val Ile Ser Ala Leu Leu Leu Leu Gly Val Leu Ala Glu
    290                 295                 300

Ile Ala Ser Trp Ile Val Gly Pro Ser Arg Gly Met Tyr Val Thr Ala
305                 310                 315                 320
```

Gln Lys Asn Leu Leu Pro Ala Ala Phe Ala Lys Met Asn Lys Asn Gly
                325                 330                 335

Val Pro Val Thr Leu Val Ile Ser Gln Leu Val Ile Thr Ser Ile Ala
            340                 345                 350

Leu Ile Ile Leu Thr Asn Thr Gly Gly Asn Asn Met Ser Phe Leu
            355                 360                 365

Ile Ala Leu Ala Leu Thr Val Val Ile Tyr Leu Cys Ala Tyr Phe Met
370                 375                 380

Leu Phe Ile Gly Tyr Ile Val Leu Val Leu Lys His Pro Asp Leu Lys
385                 390                 395                 400

Arg Thr Phe Asn Ile Pro Gly Gly Lys Gly Val Lys Leu Val Val Ala
                405                 410                 415

Ile Val Gly Leu Leu Thr Ser Ile Met Ala Phe Ile Val Ser Phe Leu
            420                 425                 430

Pro Pro Asp Asn Ile Gln Gly Asp Ser Thr Asp Met Tyr Val Glu Leu
            435                 440                 445

Leu Val Val Ser Phe Leu Val Val Leu Ala Leu Pro Phe Ile Leu Tyr
450                 455                 460

Ala Val His Asp Arg Lys Gly Lys Ala Asn Thr Gly Val Thr Leu Glu
465                 470                 475                 480

Pro Ile Asn Ser Gln Asn Ala Pro Lys Gly His Phe Phe Leu His Pro
                485                 490                 495

Arg Ala Arg Ser Pro His Tyr Ile Val Met Asn Asp Lys Lys His
            500                 505                 510

<210> SEQ ID NO 7
<211> LENGTH: 344
<212> TYPE: DNA
<213> ORGANISM: Escherichia coli

<400> SEQUENCE: 7
aagctttacg cgaacgagcc atgacattgc tgacgactct ggcagtggca gatgacataa      60
aactggtcga ctggttacaa caacgcctgg ggcttttaga gcaacgagac acggcaatgt     120
tgcaccgttt gctgcatgat attgaaaaaa atatcaccaa ataaaaaacg ccttagtaag     180
tatttttcag cttttcattc tgactgcaac gggcaatatg tctctgtgtg gattaaaaaa     240
agagtgtctg atagcagctt ctgaactggt tacctgccgt gagtaaatta aaatttatt      300 gacttaggtc actaaatact ttaaccaata taggcgactc taga                      344

<210> SEQ ID NO 8
<211> LENGTH: 30
<212> TYPE: DNA
<213> ORGANISM: Artificial
<220> FEATURE:
<223> OTHER INFORMATION: gadA primer 1

<400> SEQUENCE: 8
agcccgggat ggaccagaag ctgttaacgg                                       30

<210> SEQ ID NO 9
<211> LENGTH: 32
<212> TYPE: DNA
<213> ORGANISM: Artificial
<220> FEATURE:
<223> OTHER INFORMATION: gadA primer 2

<400> SEQUENCE: 9
ccgagctctt ttttaaagg ctgggcattc gg                                     32

<210> SEQ ID NO 10
<211> LENGTH: 30
<212> TYPE: DNA
<213> ORGANISM: Artificial
<220> FEATURE:
<223> OTHER INFORMATION: gadBC primer 1

<400> SEQUENCE: 10
ttcccgggat ggataagaag caagtaacgg         30

<210> SEQ ID NO 11
<211> LENGTH: 26
<212> TYPE: DNA
<213> ORGANISM: Artificial
<220> FEATURE:
<223> OTHER INFORMATION: gadBC primer 2

<400> SEQUENCE: 11
gagagctcaa ttatcgctcc cttgtc            26

<210> SEQ ID NO 12
<211> LENGTH: 2148
<212> TYPE: DNA
<213> ORGANISM: Escherichia coli
<220> FEATURE:
<221> NAME/KEY: CDS
<222> LOCATION: (1)..(2145)

<400> SEQUENCE: 12

```
atg aac gtt att gca ata ttg aat cac atg ggg gtt tat ttt aaa gaa    48
Met Asn Val Ile Ala Ile Leu Asn His Met Gly Val Tyr Phe Lys Glu
 1               5                  10                  15 gaa ccc atc cgt gaa ctt cat cgc gcg ctt gaa cgt ctg aac ttc cag    96
Glu Pro Ile Arg Glu Leu His Arg Ala Leu Glu Arg Leu Asn Phe Gln
             20                  25                  30 att gtt tac ccg aac gac cgt gac gac tta tta aaa ctg atc gaa aac   144
Ile Val Tyr Pro Asn Asp Arg Asp Asp Leu Leu Lys Leu Ile Glu Asn
         35                  40                  45 aat gcg cgt ctg tgc ggc gtt att ttt gac tgg gat aaa tat aat ctc   192
Asn Ala Arg Leu Cys Gly Val Ile Phe Asp Trp Asp Lys Tyr Asn Leu
     50                  55                  60 gag ctg tgc gaa gaa att agc aaa atg aac gag aac ctg ccg ttg tac   240
Glu Leu Cys Glu Glu Ile Ser Lys Met Asn Glu Asn Leu Pro Leu Tyr
 65                  70                  75                  80 gcg ttc gct aat acg tat tcc act ctc gat gta agc ctg aat gac ctg   288
Ala Phe Ala Asn Thr Tyr Ser Thr Leu Asp Val Ser Leu Asn Asp Leu
                 85                  90                  95 cgt tta cag att agc ttc ttt gaa tat gcg ctg ggt gct gct gaa gat   336
Arg Leu Gln Ile Ser Phe Phe Glu Tyr Ala Leu Gly Ala Ala Glu Asp
            100                 105                 110 att gct aat aag atc aag cag acc act gac gaa tat atc aac act att   384
Ile Ala Asn Lys Ile Lys Gln Thr Thr Asp Glu Tyr Ile Asn Thr Ile
        115                 120                 125 ctg cct ccg ctg act aaa gca ctg ttt aaa tat gtt cgt gaa ggt aaa   432
Leu Pro Pro Leu Thr Lys Ala Leu Phe Lys Tyr Val Arg Glu Gly Lys
    130                 135                 140 tat act ttc tgt act cct ggt cac atg ggc ggt act gca ttc cag aaa   480
Tyr Thr Phe Cys Thr Pro Gly His Met Gly Gly Thr Ala Phe Gln Lys
145                 150                 155                 160 agc ccg gta ggt agc ctg ttc tat gat ttc ttt ggt ccg aat acc atg   528
Ser Pro Val Gly Ser Leu Phe Tyr Asp Phe Phe Gly Pro Asn Thr Met
                165                 170                 175
```

```
aaa tct gat att tcc att tca gta tct gaa ctg ggt tct ctg ctg gat    576
Lys Ser Asp Ile Ser Ile Ser Val Ser Glu Leu Gly Ser Leu Leu Asp
            180                 185                 190 cac agt ggt cca cac aaa gaa gca gaa cag tat atc gct cgc gtc ttt    624
His Ser Gly Pro His Lys Glu Ala Glu Gln Tyr Ile Ala Arg Val Phe
        195                 200                 205 aac gca gac cgc agc tac atg gtg acc aac ggt act tcc act gcg aac    672
Asn Ala Asp Arg Ser Tyr Met Val Thr Asn Gly Thr Ser Thr Ala Asn
    210                 215                 220 aaa att gtt ggt atg tac tct gct cca gca ggc agc acc att ctg att    720
Lys Ile Val Gly Met Tyr Ser Ala Pro Ala Gly Ser Thr Ile Leu Ile
225                 230                 235                 240 gac cgt aac tgc cac aaa tcg ctg acc cac ctg atg atg atg agc gat    768
Asp Arg Asn Cys His Lys Ser Leu Thr His Leu Met Met Met Ser Asp
            245                 250                 255 gtt acg cca atc tat ttc cgc ccg acc cgt aac gct tac ggt att ctt    816
Val Thr Pro Ile Tyr Phe Arg Pro Thr Arg Asn Ala Tyr Gly Ile Leu
        260                 265                 270 ggt ggt atc cca cag agt gaa ttc cag cac gct acc att gct aag cgc    864
Gly Gly Ile Pro Gln Ser Glu Phe Gln His Ala Thr Ile Ala Lys Arg
    275                 280                 285 gtg aaa gaa aca cca aac gca acc tgg ccg gta cat gct gta att acc    912
Val Lys Glu Thr Pro Asn Ala Thr Trp Pro Val His Ala Val Ile Thr
290                 295                 300 aac tct acc tat gat ggt ctg ctg tac aac acc gac ttc atc aag aaa    960
Asn Ser Thr Tyr Asp Gly Leu Leu Tyr Asn Thr Asp Phe Ile Lys Lys
305                 310                 315                 320 aca ctg gat gtg aaa tcc atc cac ttt gac tcc gcg tgg gtg cct tac   1008
Thr Leu Asp Val Lys Ser Ile His Phe Asp Ser Ala Trp Val Pro Tyr
            325                 330                 335 acc aac ttc tca ccg att tac gaa ggt aaa tgc ggt atg agc ggt ggc   1056
Thr Asn Phe Ser Pro Ile Tyr Glu Gly Lys Cys Gly Met Ser Gly Gly
        340                 345                 350 cgt gta gaa ggg aaa gtg att tac gaa acc cag tcc act cac aaa ctg   1104
Arg Val Glu Gly Lys Val Ile Tyr Glu Thr Gln Ser Thr His Lys Leu
    355                 360                 365 ctg gcg gcg ttc tct cag gct tcc atg atc cac gtt aaa ggt gac gta   1152
Leu Ala Ala Phe Ser Gln Ala Ser Met Ile His Val Lys Gly Asp Val
370                 375                 380 aac gaa gaa acc ttt aac gaa gcc tac atg atg cac acc acc act tct   1200
Asn Glu Glu Thr Phe Asn Glu Ala Tyr Met Met His Thr Thr Thr Ser
385                 390                 395                 400 ccg cac tac ggt atc gtg gcg tcc act gaa acc gct gcg gcg atg atg   1248
Pro His Tyr Gly Ile Val Ala Ser Thr Glu Thr Ala Ala Ala Met Met
            405                 410                 415 aaa ggc aat gca ggt aag cgt ctg atc aac ggt tct att gaa cgt gcg   1296
Lys Gly Asn Ala Gly Lys Arg Leu Ile Asn Gly Ser Ile Glu Arg Ala
        420                 425                 430 atc aaa ttc cgt aaa gag atc aaa cgt ctg aga acg gaa tct gat ggc   1344
Ile Lys Phe Arg Lys Glu Ile Lys Arg Leu Arg Thr Glu Ser Asp Gly
    435                 440                 445 tgg ttc ttt gat gta tgg cag ccg gat cat atc gat acg act gaa tgc   1392
Trp Phe Phe Asp Val Trp Gln Pro Asp His Ile Asp Thr Thr Glu Cys
450                 455                 460 tgg ccg ctg cgt tct gac agc acc tgg cac ggc ttc aaa aac atc gat   1440
Trp Pro Leu Arg Ser Asp Ser Thr Trp His Gly Phe Lys Asn Ile Asp
465                 470                 475                 480 aac gag cac atg tat ctt gac ccg atc aaa gtc acc ctg ctg act ccg   1488
Asn Glu His Met Tyr Leu Asp Pro Ile Lys Val Thr Leu Leu Thr Pro
            485                 490                 495
```

```
ggg atg gaa aaa gac ggc acc atg agc gac ttt ggt att ccg gcc agc    1536
Gly Met Glu Lys Asp Gly Thr Met Ser Asp Phe Gly Ile Pro Ala Ser
    500                 505                 510 atc gtg gcg aaa tac ctc gac gaa cat ggc atc gtt gtt gag aaa acc    1584
Ile Val Ala Lys Tyr Leu Asp Glu His Gly Ile Val Val Glu Lys Thr
515                 520                 525 ggt ccg tat aac ctg ctg ttc ctg ttc agc atc ggt atc gat aag acc    1632
Gly Pro Tyr Asn Leu Leu Phe Leu Phe Ser Ile Gly Ile Asp Lys Thr
530                 535                 540 aaa gca ctg agc ctg ctg cgt gct ctg act gac ttt aaa cgt gcg ttc    1680
Lys Ala Leu Ser Leu Leu Arg Ala Leu Thr Asp Phe Lys Arg Ala Phe
545                 550                 555                 560 gac ctg aac ctg cgt gtg aaa aac atg ctg ccg tct ctg tat cgt gaa    1728
Asp Leu Asn Leu Arg Val Lys Asn Met Leu Pro Ser Leu Tyr Arg Glu
                565                 570                 575 gat cct gaa ttc tat gaa aac atg cgt att cag gaa ctg gct cag aat    1776
Asp Pro Glu Phe Tyr Glu Asn Met Arg Ile Gln Glu Leu Ala Gln Asn
            580                 585                 590 atc cac aaa ctg att gtt cac cac aat ctg ccg gat ctg atg tat cgc    1824
Ile His Lys Leu Ile Val His His Asn Leu Pro Asp Leu Met Tyr Arg
        595                 600                 605 gca ttt gaa gtg ctg ccg acg atg gta atg act ccg tat gct gca ttc    1872
Ala Phe Glu Val Leu Pro Thr Met Val Met Thr Pro Tyr Ala Ala Phe
    610                 615                 620 cag aaa gag ctg cac ggt atg acc gaa gaa gtt tac ctc gac gaa atg    1920
Gln Lys Glu Leu His Gly Met Thr Glu Glu Val Tyr Leu Asp Glu Met
625                 630                 635                 640 gta ggt cgt att aac gcc aat atg atc ctt ccg tac ccg ccg gga gtt    1968
Val Gly Arg Ile Asn Ala Asn Met Ile Leu Pro Tyr Pro Pro Gly Val
                645                 650                 655 cct ctg gta atg ccg ggt gaa atg atc acc gaa gaa agc cgt ccg gtt    2016
Pro Leu Val Met Pro Gly Glu Met Ile Thr Glu Glu Ser Arg Pro Val
            660                 665                 670 ctg gag ttc ctg cag atg ctg tgt gaa atc ggc gct cac tat ccg ggc    2064
Leu Glu Phe Leu Gln Met Leu Cys Glu Ile Gly Ala His Tyr Pro Gly
        675                 680                 685 ttt gaa acc gat att cac ggt gca tac cgt cag gct gat ggc cgc tat    2112
Phe Glu Thr Asp Ile His Gly Ala Tyr Arg Gln Ala Asp Gly Arg Tyr
    690                 695                 700 acc gtt aag gta ttg aaa gaa gaa agc aaa aaa taa                    2148
Thr Val Lys Val Leu Lys Glu Glu Ser Lys Lys
705                 710                 715

<210> SEQ ID NO 13
<211> LENGTH: 715
<212> TYPE: PRT
<213> ORGANISM: Escherichia coli

<400> SEQUENCE: 13

Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
            20                  25                  30

Ile Val Tyr Pro Asn Asp Arg Asp Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
```

```
                    85                  90                  95
Arg Leu Gln Ile Ser Phe Phe Glu Tyr Ala Leu Gly Ala Ala Glu Asp
                100                 105                 110

Ile Ala Asn Lys Ile Lys Gln Thr Thr Asp Glu Tyr Ile Asn Thr Ile
                115                 120                 125

Leu Pro Pro Leu Thr Lys Ala Leu Phe Lys Tyr Val Arg Glu Gly Lys
            130                 135                 140

Tyr Thr Phe Cys Thr Pro Gly His Met Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
                180                 185                 190

His Ser Gly Pro His Lys Glu Ala Glu Gln Tyr Ile Ala Arg Val Phe
            195                 200                 205

Asn Ala Asp Arg Ser Tyr Met Val Thr Asn Gly Thr Ser Thr Ala Asn
210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255

Val Thr Pro Ile Tyr Phe Arg Pro Thr Arg Asn Ala Tyr Gly Ile Leu
                260                 265                 270

Gly Gly Ile Pro Gln Ser Glu Phe Gln His Ala Thr Ile Ala Lys Arg
            275                 280                 285

Val Lys Glu Thr Pro Asn Ala Thr Trp Pro Val His Ala Val Ile Thr
        290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
            340                 345                 350

Arg Val Glu Gly Lys Val Ile Tyr Glu Thr Gln Ser Thr His Lys Leu
        355                 360                 365

Leu Ala Ala Phe Ser Gln Ala Ser Met Ile His Val Lys Gly Asp Val
        370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                405                 410                 415

Lys Gly Asn Ala Gly Lys Arg Leu Ile Asn Gly Ser Ile Glu Arg Ala
            420                 425                 430

Ile Lys Phe Arg Lys Glu Ile Lys Arg Leu Arg Thr Glu Ser Asp Gly
        435                 440                 445

Trp Phe Phe Asp Val Trp Gln Pro Asp His Ile Asp Thr Thr Glu Cys
450                 455                 460

Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Glu Lys Asp Gly Thr Met Ser Asp Phe Gly Ile Pro Ala Ser
            500                 505                 510
```

```
Ile Val Ala Lys Tyr Leu Asp Glu His Gly Ile Val Val Glu Lys Thr
            515                 520                 525
Gly Pro Tyr Asn Leu Leu Phe Leu Phe Ser Ile Gly Ile Asp Lys Thr
        530                 535                 540
Lys Ala Leu Ser Leu Leu Arg Ala Leu Thr Asp Phe Lys Arg Ala Phe
545                 550                 555                 560
Asp Leu Asn Leu Arg Val Lys Asn Met Leu Pro Ser Leu Tyr Arg Glu
                565                 570                 575
Asp Pro Glu Phe Tyr Glu Asn Met Arg Ile Gln Glu Leu Ala Gln Asn
            580                 585                 590
Ile His Lys Leu Ile Val His His Asn Leu Pro Asp Leu Met Tyr Arg
        595                 600                 605
Ala Phe Glu Val Leu Pro Thr Met Val Met Thr Pro Tyr Ala Ala Phe
    610                 615                 620
Gln Lys Glu Leu His Gly Met Thr Glu Glu Val Tyr Leu Asp Glu Met
625                 630                 635                 640
Val Gly Arg Ile Asn Ala Asn Met Ile Leu Pro Tyr Pro Pro Gly Val
                645                 650                 655
Pro Leu Val Met Pro Gly Glu Met Ile Thr Glu Glu Ser Arg Pro Val
            660                 665                 670
Leu Glu Phe Leu Gln Met Leu Cys Glu Ile Gly Ala His Tyr Pro Gly
        675                 680                 685
Phe Glu Thr Asp Ile His Gly Ala Tyr Arg Gln Ala Asp Gly Arg Tyr
    690                 695                 700
Thr Val Lys Val Leu Lys Glu Glu Ser Lys Lys
705                 710                 715

<210> SEQ ID NO 14
<211> LENGTH: 2142
<212> TYPE: DNA
<213> ORGANISM: Escherichia coli
<220> FEATURE:
<221> NAME/KEY: CDS
<222> LOCATION: (1)..(2139)

<400> SEQUENCE: 14 atg aac atc att gcc att atg gga ccg cat ggc gtc ttt tat aaa gat      48
Met Asn Ile Ile Ala Ile Met Gly Pro His Gly Val Phe Tyr Lys Asp
1               5                   10                  15 gag ccc atc aaa gaa ctg gag tcg gcg ctg gtg gcg caa ggc ttt cag      96
Glu Pro Ile Lys Glu Leu Glu Ser Ala Leu Val Ala Gln Gly Phe Gln
                20                  25                  30 att atc tgg cca caa aac agc gtt gat ttg ctg aaa ttt atc gag cat     144
Ile Ile Trp Pro Gln Asn Ser Val Asp Leu Leu Lys Phe Ile Glu His
            35                  40                  45 aac cct cga att tgc ggc gtg att ttt gac tgg gat gag tac agt ctc     192
Asn Pro Arg Ile Cys Gly Val Ile Phe Asp Trp Asp Glu Tyr Ser Leu
        50                  55                  60 gat tta tgt agc gat atc aat cag ctt aat gaa tat ctc ccg ctt tat     240
Asp Leu Cys Ser Asp Ile Asn Gln Leu Asn Glu Tyr Leu Pro Leu Tyr
65                  70                  75                  80 gcc ttc atc aac acc cac tcg acg atg gat gtc agc gtg cag gat atg     288
Ala Phe Ile Asn Thr His Ser Thr Met Asp Val Ser Val Gln Asp Met
                85                  90                  95 cgg atg gcg ctc tgg ttt ttt gaa tat gcg ctg ggg cag gcg gaa gat     336
Arg Met Ala Leu Trp Phe Phe Glu Tyr Ala Leu Gly Gln Ala Glu Asp
                100                 105                 110 atc gcc att cgt atg cgt cag tac acc gac gaa tat ctt gat aac att     384
Ile Ala Ile Arg Met Arg Gln Tyr Thr Asp Glu Tyr Leu Asp Asn Ile
```

```
                    115                 120                     125
aca ccg ccg ttc acg aaa gcc ttg ttt acc tac gtc aaa gag cgg aag       432
Thr Pro Pro Phe Thr Lys Ala Leu Phe Thr Tyr Val Lys Glu Arg Lys
    130                 135                 140 tac acc ttt tgt acg ccg ggg cat atg ggc ggc acc gca tat caa aaa       480
Tyr Thr Phe Cys Thr Pro Gly His Met Gly Gly Thr Ala Tyr Gln Lys
145                 150                 155                 160 agc ccg gtt ggc tgt ctg ttt tat gat ttt ttc ggc ggg aat act ctt       528
Ser Pro Val Gly Cys Leu Phe Tyr Asp Phe Phe Gly Gly Asn Thr Leu
                165                 170                 175 aag gct gat gtc tct att tcg gtc acc gag ctt ggt tcg ttg ctc gac       576
Lys Ala Asp Val Ser Ile Ser Val Thr Glu Leu Gly Ser Leu Leu Asp
            180                 185                 190 cac acc ggg cca cac ctg gaa gcg gaa gag tac atc gcg cgg act ttt       624
His Thr Gly Pro His Leu Glu Ala Glu Glu Tyr Ile Ala Arg Thr Phe
        195                 200                 205 ggc gcg gaa cag agt tat atc gtt acc aac gga aca tcg acg tcg aac       672
Gly Ala Glu Gln Ser Tyr Ile Val Thr Asn Gly Thr Ser Thr Ser Asn
    210                 215                 220 aaa att gtg ggt atg tac gcc gcg cca tcc ggc agt acg ctg ttg atc       720
Lys Ile Val Gly Met Tyr Ala Ala Pro Ser Gly Ser Thr Leu Leu Ile
225                 230                 235                 240 gac cgc aat tgt cat aaa tcg ctg gcg cat ctg ttg atg atg aac gat       768
Asp Arg Asn Cys His Lys Ser Leu Ala His Leu Leu Met Met Asn Asp
                245                 250                 255 gta gtg cca gtc tgg ctg aaa ccg acg cgt aat gcg ttg ggg att ctt       816
Val Val Pro Val Trp Leu Lys Pro Thr Arg Asn Ala Leu Gly Ile Leu
            260                 265                 270 ggt ggg atc ccg cgc cgt gaa ttt act cgc gac agc atc gaa gag aaa       864
Gly Gly Ile Pro Arg Arg Glu Phe Thr Arg Asp Ser Ile Glu Glu Lys
        275                 280                 285 gtc gct gct acc acg caa gca caa tgg ccg gtt cat gcg gtg atc acc       912
Val Ala Ala Thr Thr Gln Ala Gln Trp Pro Val His Ala Val Ile Thr
    290                 295                 300 aac tcc acc tat gat ggc ttg ctc tac aac acc gac tgg atc aaa cag       960
Asn Ser Thr Tyr Asp Gly Leu Leu Tyr Asn Thr Asp Trp Ile Lys Gln
305                 310                 315                 320 acg ctg gat gtc ccg tcg att cac ttc gat tct gcc tgg gtg ccg tac      1008
Thr Leu Asp Val Pro Ser Ile His Phe Asp Ser Ala Trp Val Pro Tyr
                325                 330                 335 acc cat ttt cat ccg atc tac cag ggt aaa agt ggt atg agc ggc gag      1056
Thr His Phe His Pro Ile Tyr Gln Gly Lys Ser Gly Met Ser Gly Glu
            340                 345                 350 cgt gtt gcg gga aaa gtg atc ttc gaa acg caa tcg acc cac aaa atg      1104
Arg Val Ala Gly Lys Val Ile Phe Glu Thr Gln Ser Thr His Lys Met
        355                 360                 365 ctg gcg gcg tta tcg cag gct tcg ctg atc cac att aaa ggc gag tat      1152
Leu Ala Ala Leu Ser Gln Ala Ser Leu Ile His Ile Lys Gly Glu Tyr
    370                 375                 380 gac gaa gag gcc ttt aac gaa gcc ttt atg atg cat acc acc acc tcg      1200
Asp Glu Glu Ala Phe Asn Glu Ala Phe Met Met His Thr Thr Thr Ser
385                 390                 395                 400 ccc agt tat ccc att gtt gct tcg gtt gag acg gcg gcg gcg atg ctg      1248
Pro Ser Tyr Pro Ile Val Ala Ser Val Glu Thr Ala Ala Ala Met Leu
                405                 410                 415 cgt ggt aat ccg ggc aaa cgg ctg att aac cgt tca gta gaa cga gct      1296
Arg Gly Asn Pro Gly Lys Arg Leu Ile Asn Arg Ser Val Glu Arg Ala
            420                 425                 430 ctg cat ttt cgc aaa gag gtc cag cgg ctg cgg gaa gag tct gac ggt      1344
Leu His Phe Arg Lys Glu Val Gln Arg Leu Arg Glu Glu Ser Asp Gly
```

```
                435                 440                 445
tgg ttt ttc gat atc tgg caa ccg ccg cag gtg gat gaa gcc gaa tgc      1392
Trp Phe Phe Asp Ile Trp Gln Pro Pro Gln Val Asp Glu Ala Glu Cys
450                 455                 460 tgg ccc gtt gcg cct ggc gaa cag tgg cac ggc ttt aac gat gcg gat      1440
Trp Pro Val Ala Pro Gly Glu Gln Trp His Gly Phe Asn Asp Ala Asp
465                 470                 475                 480 gcc gat cat atg ttt ctc gat ccg gtt aaa gtc act att ttg aca ccg      1488
Ala Asp His Met Phe Leu Asp Pro Val Lys Val Thr Ile Leu Thr Pro
            485                 490                 495 ggg atg gac gag cag ggc aat atg agc gag gag ggg atc ccg gcg gcg      1536
Gly Met Asp Glu Gln Gly Asn Met Ser Glu Glu Gly Ile Pro Ala Ala
        500                 505                 510 ctg gta gca aaa ttc ctc gac gaa cgt ggg atc gta gta gag aaa acc      1584
Leu Val Ala Lys Phe Leu Asp Glu Arg Gly Ile Val Val Glu Lys Thr
    515                 520                 525 ggc cct tat aac ctg ctg ttt ctc ttt agt att ggc atc gat aaa acc      1632
Gly Pro Tyr Asn Leu Leu Phe Leu Phe Ser Ile Gly Ile Asp Lys Thr
530                 535                 540 aaa gca atg gga tta ttg cgt ggg ttg acg gaa ttc aaa cgc tct tac      1680
Lys Ala Met Gly Leu Leu Arg Gly Leu Thr Glu Phe Lys Arg Ser Tyr
545                 550                 555                 560 gat ctc aac ctg cgg atc aaa aat atg cta ccc gat ctc tat gca gaa      1728
Asp Leu Asn Leu Arg Ile Lys Asn Met Leu Pro Asp Leu Tyr Ala Glu
            565                 570                 575 gat ccc gat ttc tac cgc aat atg cgt att cag gat ctg gca caa ggg      1776
Asp Pro Asp Phe Tyr Arg Asn Met Arg Ile Gln Asp Leu Ala Gln Gly
        580                 585                 590 atc cat aag ctg att cgt aaa cac gat ctt ccc ggt ttg atg ttg cgg      1824
Ile His Lys Leu Ile Arg Lys His Asp Leu Pro Gly Leu Met Leu Arg
    595                 600                 605 gca ttc gat act ttg ccg gag atg atc atg acg cca cat cag gca tgg      1872
Ala Phe Asp Thr Leu Pro Glu Met Ile Met Thr Pro His Gln Ala Trp
610                 615                 620 caa cga caa att aaa ggc gaa gta gaa acc att gcg ctg gaa caa ctg      1920
Gln Arg Gln Ile Lys Gly Glu Val Glu Thr Ile Ala Leu Glu Gln Leu
625                 630                 635                 640 gtc ggt aga gta tcg gca aat atg atc ctg cct tat cca ccg ggc gta      1968
Val Gly Arg Val Ser Ala Asn Met Ile Leu Pro Tyr Pro Pro Gly Val
            645                 650                 655 ccg ctg ttg atg cct gga gaa atg ctg acc aaa gag agc cgc aca gta      2016
Pro Leu Leu Met Pro Gly Glu Met Leu Thr Lys Glu Ser Arg Thr Val
        660                 665                 670 ctc gat ttt cta ctg atg ctt tgt tcc gtc ggg caa cat tac ccc ggt      2064
Leu Asp Phe Leu Leu Met Leu Cys Ser Val Gly Gln His Tyr Pro Gly
    675                 680                 685 ttt gaa acg gat att cac ggc gcg aaa cag gac gaa gac ggc gtt tac      2112
Phe Glu Thr Asp Ile His Gly Ala Lys Gln Asp Glu Asp Gly Val Tyr
690                 695                 700 cgc gta cga gtc cta aaa atg gcg gga taa                              2142
Arg Val Arg Val Leu Lys Met Ala Gly
705                 710

<210> SEQ ID NO 15
<211> LENGTH: 713
<212> TYPE: PRT
<213> ORGANISM: Escherichia coli

<400> SEQUENCE: 15

Met Asn Ile Ile Ala Ile Met Gly Pro His Gly Val Phe Tyr Lys Asp
1               5                   10                  15
```

-continued

Glu Pro Ile Lys Glu Leu Glu Ser Ala Leu Val Ala Gln Gly Phe Gln
            20                  25                  30

Ile Ile Trp Pro Gln Asn Ser Val Asp Leu Leu Lys Phe Ile Glu His
            35                  40                  45

Asn Pro Arg Ile Cys Gly Val Ile Phe Asp Trp Asp Glu Tyr Ser Leu
    50                  55                  60

Asp Leu Cys Ser Asp Ile Asn Gln Leu Asn Glu Tyr Leu Pro Leu Tyr
65                  70                  75                  80

Ala Phe Ile Asn Thr His Ser Thr Met Asp Val Ser Val Gln Asp Met
                    85                  90                  95

Arg Met Ala Leu Trp Phe Phe Glu Tyr Ala Leu Gly Gln Ala Glu Asp
                100                 105                 110

Ile Ala Ile Arg Met Arg Gln Tyr Thr Asp Glu Tyr Leu Asp Asn Ile
                115                 120                 125

Thr Pro Pro Phe Thr Lys Ala Leu Phe Thr Tyr Val Lys Glu Arg Lys
    130                 135                 140

Tyr Thr Phe Cys Thr Pro Gly His Met Gly Gly Thr Ala Tyr Gln Lys
145                 150                 155                 160

Ser Pro Val Gly Cys Leu Phe Tyr Asp Phe Phe Gly Gly Asn Thr Leu
                165                 170                 175

Lys Ala Asp Val Ser Ile Ser Val Thr Glu Leu Gly Ser Leu Leu Asp
                180                 185                 190

His Thr Gly Pro His Leu Glu Ala Glu Glu Tyr Ile Ala Arg Thr Phe
            195                 200                 205

Gly Ala Glu Gln Ser Tyr Ile Val Thr Asn Gly Thr Ser Thr Ser Asn
    210                 215                 220

Lys Ile Val Gly Met Tyr Ala Ala Pro Ser Gly Ser Thr Leu Leu Ile
225                 230                 235                 240

Asp Arg Asn Cys His Lys Ser Leu Ala His Leu Leu Met Met Asn Asp
                245                 250                 255

Val Val Pro Val Trp Leu Lys Pro Thr Arg Asn Ala Leu Gly Ile Leu
                260                 265                 270

Gly Gly Ile Pro Arg Arg Glu Phe Thr Arg Asp Ser Ile Glu Glu Lys
        275                 280                 285

Val Ala Ala Thr Thr Gln Ala Gln Trp Pro Val His Ala Val Ile Thr
    290                 295                 300

Asn Ser Thr Tyr Asp Gly Leu Leu Tyr Asn Thr Asp Trp Ile Lys Gln
305                 310                 315                 320

Thr Leu Asp Val Pro Ser Ile His Phe Asp Ser Ala Trp Val Pro Tyr
                325                 330                 335

Thr His Phe His Pro Ile Tyr Gln Gly Lys Ser Gly Met Ser Gly Glu
            340                 345                 350

Arg Val Ala Gly Lys Val Ile Phe Glu Thr Gln Ser Thr His Lys Met
        355                 360                 365

Leu Ala Ala Leu Ser Gln Ala Ser Leu Ile His Ile Lys Gly Glu Tyr
    370                 375                 380

Asp Glu Glu Ala Phe Asn Glu Ala Phe Met Met His Thr Thr Thr Ser
385                 390                 395                 400

Pro Ser Tyr Pro Ile Val Ala Ser Val Glu Thr Ala Ala Ala Met Leu
                405                 410                 415

Arg Gly Asn Pro Gly Lys Arg Leu Ile Asn Arg Ser Val Glu Arg Ala
                420                 425                 430

Leu His Phe Arg Lys Glu Val Gln Arg Leu Arg Glu Glu Ser Asp Gly

```
                435            440            445
Trp Phe Phe Asp Ile Trp Gln Pro Pro Gln Val Asp Glu Ala Glu Cys
450                 455                 460

Trp Pro Val Ala Pro Gly Glu Gln Trp His Gly Phe Asn Asp Ala Asp
465                 470                 475                 480

Ala Asp His Met Phe Leu Asp Pro Val Lys Val Thr Ile Leu Thr Pro
                485                 490                 495

Gly Met Asp Glu Gln Gly Asn Met Ser Glu Gly Ile Pro Ala Ala
            500                 505                 510

Leu Val Ala Lys Phe Leu Asp Glu Arg Gly Ile Val Val Glu Lys Thr
            515                 520                 525

Gly Pro Tyr Asn Leu Leu Phe Leu Phe Ser Ile Gly Ile Asp Lys Thr
            530                 535                 540

Lys Ala Met Gly Leu Leu Arg Gly Leu Thr Glu Phe Lys Arg Ser Tyr
545                 550                 555                 560

Asp Leu Asn Leu Arg Ile Lys Asn Met Leu Pro Asp Leu Tyr Ala Glu
                565                 570                 575

Asp Pro Asp Phe Tyr Arg Asn Met Arg Ile Gln Asp Leu Ala Gln Gly
                580                 585                 590

Ile His Lys Leu Ile Arg Lys His Asp Leu Pro Gly Leu Met Leu Arg
                595                 600                 605

Ala Phe Asp Thr Leu Pro Glu Met Ile Met Thr Pro His Gln Ala Trp
610                 615                 620

Gln Arg Gln Ile Lys Gly Glu Val Glu Thr Ile Ala Leu Glu Gln Leu
625                 630                 635                 640

Val Gly Arg Val Ser Ala Asn Met Ile Leu Pro Tyr Pro Pro Gly Val
                645                 650                 655

Pro Leu Leu Met Pro Gly Glu Met Leu Thr Lys Glu Ser Arg Thr Val
                660                 665                 670

Leu Asp Phe Leu Leu Met Leu Cys Ser Val Gly Gln His Tyr Pro Gly
                675                 680                 685

Phe Glu Thr Asp Ile His Gly Ala Lys Gln Asp Glu Asp Gly Val Tyr
                690                 695                 700

Arg Val Arg Val Leu Lys Met Ala Gly
705                 710

<210> SEQ ID NO 16
<211> LENGTH: 54
<212> TYPE: DNA
<213> ORGANISM: Artificial sequence
<220> FEATURE:
<223> OTHER INFORMATION: 5'-primer for cadA

<400> SEQUENCE: 16
tttgctttct ctttcaata ccttaacggt atagcgtgaa gcctgctttt ttat            54

<210> SEQ ID NO 17
<211> LENGTH: 54
<212> TYPE: DNA
<213> ORGANISM: Artificial sequence
<220> FEATURE:
<223> OTHER INFORMATION: 3'-primer for cadA

<400> SEQUENCE: 17
agatatgact atgaacgtta ttgcaatatt gaatcacgct caagttagta taaa            54

<210> SEQ ID NO 18
<211> LENGTH: 54
```

-continued

```
<212> TYPE: DNA
<213> ORGANISM: Artificial sequence
<220> FEATURE:
<223> OTHER INFORMATION: 5'-primer for ldc

<400> SEQUENCE: 18
ggaggaacac atgaacatca ttgccattat gggacctgaa gcctgctttt ttat        54

<210> SEQ ID NO 19
<211> LENGTH: 53
<212> TYPE: DNA
<213> ORGANISM: Artificial sequence
<220> FEATURE:
<223> OTHER INFORMATION: 3'-primer for ldc

<400> SEQUENCE: 19
cgccattttt aggactcgta cgcggtaaac gccgtccgtc aagttagtat aaa         53

<210> SEQ ID NO 20
<211> LENGTH: 20
<212> TYPE: DNA
<213> ORGANISM: Artificial sequence
<220> FEATURE:
<223> OTHER INFORMATION: gadB primer

<400> SEQUENCE: 20
tcaggtatgt ttaaagctgt                                              20

<210> SEQ ID NO 21
<211> LENGTH: 20
<212> TYPE: DNA
<213> ORGANISM: Artificial sequence
<220> FEATURE:
<223> OTHER INFORMATION: gadC primer

<400> SEQUENCE: 21
atggctacat cagtacagac                                              20

<210> SEQ ID NO 22
<211> LENGTH: 825
<212> TYPE: DNA
<213> ORGANISM: Escherichia coli
<220> FEATURE:
<221> NAME/KEY: CDS
<222> LOCATION: (1)..(825)

<400> SEQUENCE: 22 atg caa tca cta cat ggg aat tgt cta att gcg tat gca aga cat aaa    48
Met Gln Ser Leu His Gly Asn Cys Leu Ile Ala Tyr Ala Arg His Lys
1               5                   10                  15 tat att ctc acc atg gtt aat ggt gaa tat cgc tat ttt aat ggc ggt    96
Tyr Ile Leu Thr Met Val Asn Gly Glu Tyr Arg Tyr Phe Asn Gly Gly
            20                  25                  30 gac ctg gtt ttt gcg gat gca agc caa att cga gta gat aag tgt gtt  144
Asp Leu Val Phe Ala Asp Ala Ser Gln Ile Arg Val Asp Lys Cys Val
        35                  40                  45 gaa aat ttt gta ttc gtg tca agg gac acg ctt tca tta ttt ctc ccg  192
Glu Asn Phe Val Phe Val Ser Arg Asp Thr Leu Ser Leu Phe Leu Pro
    50                  55                  60 atg ctc aag gag gag gca tta aat ctt cat gca cat aaa aaa gtt tct  240
Met Leu Lys Glu Glu Ala Leu Asn Leu His Ala His Lys Lys Val Ser
65                  70                  75                  80 tca tta ctc gtt cat cac tgt agt aga gat att cct gtt ttt cag gaa  288
Ser Leu Leu Val His His Cys Ser Arg Asp Ile Pro Val Phe Gln Glu
                85                  90                  95
```

```
gtt gcg caa cta tcg cag aat aag aat ctt cgc tat gca gaa atg cta        336
Val Ala Gln Leu Ser Gln Asn Lys Asn Leu Arg Tyr Ala Glu Met Leu
            100                 105                 110 cgt aaa aga gca tta atc ttt gcg ttg tta tct gtt ttt ctt gag gat        384
Arg Lys Arg Ala Leu Ile Phe Ala Leu Leu Ser Val Phe Leu Glu Asp
        115                 120                 125 gag cac ttt ata ccg ctg ctt ctg aac gtt tta caa ccg aac atg cga        432
Glu His Phe Ile Pro Leu Leu Leu Asn Val Leu Gln Pro Asn Met Arg
    130                 135                 140 aca cga gtt tgt acg gtt atc aat aat aat atc gcc cat gag tgg aca        480
Thr Arg Val Cys Thr Val Ile Asn Asn Asn Ile Ala His Glu Trp Thr
145                 150                 155                 160 cta gcc cga atc gcc agc gag ctg ttg atg agt cca agt ctg tta aag        528
Leu Ala Arg Ile Ala Ser Glu Leu Leu Met Ser Pro Ser Leu Leu Lys
                165                 170                 175 aaa aaa ttg cgc gaa gaa gag aca tca tat tca cag ttg ctt act gag        576
Lys Lys Leu Arg Glu Glu Glu Thr Ser Tyr Ser Gln Leu Leu Thr Glu
            180                 185                 190 tgt aga atg caa cgt gct ttg caa ctt att gtt ata cat ggt ttt tca        624
Cys Arg Met Gln Arg Ala Leu Gln Leu Ile Val Ile His Gly Phe Ser
        195                 200                 205 att aag cga gtt gca gta tcc tgt gga tat cac agc gtg tcg tat ttc        672
Ile Lys Arg Val Ala Val Ser Cys Gly Tyr His Ser Val Ser Tyr Phe
    210                 215                 220 att tac gtc ttt cga aat tat tat ggg atg acg ccc aca gag tat cag        720
Ile Tyr Val Phe Arg Asn Tyr Tyr Gly Met Thr Pro Thr Glu Tyr Gln
225                 230                 235                 240 gag cga tcg gcg cag aga ttg tcg aac cgt gac tcg gcg gca agt att        768
Glu Arg Ser Ala Gln Arg Leu Ser Asn Arg Asp Ser Ala Ala Ser Ile
                245                 250                 255 gtt gcg caa ggg aat ttt tac ggc act gac cgt tct gcg gaa gga ata        816
Val Ala Gln Gly Asn Phe Tyr Gly Thr Asp Arg Ser Ala Glu Gly Ile
            260                 265                 270 aga tta tag                                                            825
Arg Leu
```

<210> SEQ ID NO 23
<211> LENGTH: 274
<212> TYPE: PRT
<213> ORGANISM: Escherichia coli

<400> SEQUENCE: 23

```
Met Gln Ser Leu His Gly Asn Cys Leu Ile Ala Tyr Ala Arg His Lys
1               5                   10                  15

Tyr Ile Leu Thr Met Val Asn Gly Glu Tyr Arg Tyr Phe Asn Gly Gly
            20                  25                  30

Asp Leu Val Phe Ala Asp Ala Ser Gln Ile Arg Val Asp Lys Cys Val
        35                  40                  45

Glu Asn Phe Val Phe Val Ser Arg Asp Thr Leu Ser Leu Phe Leu Pro
    50                  55                  60

Met Leu Lys Glu Glu Ala Leu Asn Leu His Ala His Lys Lys Val Ser
65                  70                  75                  80

Ser Leu Leu Val His His Cys Ser Arg Asp Ile Pro Val Phe Gln Glu
                85                  90                  95

Val Ala Gln Leu Ser Gln Asn Lys Asn Leu Arg Tyr Ala Glu Met Leu
            100                 105                 110

Arg Lys Arg Ala Leu Ile Phe Ala Leu Leu Ser Val Phe Leu Glu Asp
        115                 120                 125

Glu His Phe Ile Pro Leu Leu Leu Asn Val Leu Gln Pro Asn Met Arg
```

```
                130             135             140
Thr Arg Val Cys Thr Val Ile Asn Asn Ile Ala His Glu Trp Thr
145                 150                 155                 160

Leu Ala Arg Ile Ala Ser Glu Leu Leu Met Ser Pro Ser Leu Leu Lys
                    165                 170                 175

Lys Lys Leu Arg Glu Glu Thr Ser Tyr Ser Gln Leu Leu Thr Glu
            180                 185                 190

Cys Arg Met Gln Arg Ala Leu Gln Leu Ile Val Ile His Gly Phe Ser
        195                 200                 205

Ile Lys Arg Val Ala Val Ser Cys Gly Tyr His Ser Val Ser Tyr Phe
    210                 215                 220

Ile Tyr Val Phe Arg Asn Tyr Tyr Gly Met Thr Pro Thr Glu Tyr Gln
225                 230                 235                 240

Glu Arg Ser Ala Gln Arg Leu Ser Asn Arg Asp Ser Ala Ala Ser Ile
                245                 250                 255

Val Ala Gln Gly Asn Phe Tyr Gly Thr Asp Arg Ser Ala Glu Gly Ile
            260                 265                 270

Arg Leu
```

<210> SEQ ID NO 24
<211> LENGTH: 729
<212> TYPE: DNA
<213> ORGANISM: Escherichia coli
<220> FEATURE:
<221> NAME/KEY: CDS
<222> LOCATION: (1)..(729)

<400> SEQUENCE: 24

```
atg act cat gtc tgc tcg gtg atc ctc att cgt cgt tca ttc gat att      48
Met Thr His Val Cys Ser Val Ile Leu Ile Arg Arg Ser Phe Asp Ile
1               5                   10                  15 tat cat gaa cag caa aaa ata tcg ctg cat aac gag agt att ctg ctg      96
Tyr His Glu Gln Gln Lys Ile Ser Leu His Asn Glu Ser Ile Leu Leu
            20                  25                  30 ctg gag aaa aat ttg gca gac gat ttt gcg ttt tgt tca ccg gat acg     144
Leu Glu Lys Asn Leu Ala Asp Asp Phe Ala Phe Cys Ser Pro Asp Thr
        35                  40                  45 cga cga ctg gat atc gat gag ctg aca gtt tgc cat tac tta caa aat     192
Arg Arg Leu Asp Ile Asp Glu Leu Thr Val Cys His Tyr Leu Gln Asn
50                  55                  60 att cgt cag cta cca cgc aat tta ggg tta cac agc aaa gac cgt ttg     240
Ile Arg Gln Leu Pro Arg Asn Leu Gly Leu His Ser Lys Asp Arg Leu
65                  70                  75                  80 tta att aac cag tca ccc ccc atg ccg ctg gtg acg gcg att ttt gat     288
Leu Ile Asn Gln Ser Pro Pro Met Pro Leu Val Thr Ala Ile Phe Asp
                85                  90                  95 agc ttc aat gaa tcc ggg gta aat tca ccg ata ctg agc aat atg ctc     336
Ser Phe Asn Glu Ser Gly Val Asn Ser Pro Ile Leu Ser Asn Met Leu
            100                 105                 110 tac ctt tcc tgt tta tcg atg ttt tct cat aag aaa gaa ctg atc ccc     384
Tyr Leu Ser Cys Leu Ser Met Phe Ser His Lys Lys Glu Leu Ile Pro
        115                 120                 125 tta ctt ttc aat agc atc agc act gtt tca gga aaa gtt gaa cgc ctt     432
Leu Leu Phe Asn Ser Ile Ser Thr Val Ser Gly Lys Val Glu Arg Leu
130                 135                 140 att agc ttt gat atc gcc aaa cgt tgg tat ctg cgc gat atc gcg gaa     480
Ile Ser Phe Asp Ile Ala Lys Arg Trp Tyr Leu Arg Asp Ile Ala Glu
145                 150                 155                 160 aga atg tat acc agc gag agt cta atc aaa aaa aag ttg cag gat gaa     528
```

```
Arg Met Tyr Thr Ser Glu Ser Leu Ile Lys Lys Leu Gln Asp Glu
            165                 170                 175 aat acc tgt ttc agt aaa ata tta ctc gcc tcc agg atg tcg atg gcc     576
Asn Thr Cys Phe Ser Lys Ile Leu Leu Ala Ser Arg Met Ser Met Ala
            180                 185                 190 aga cga tta ctc gag tta cgt caa att cct ctg cat act att gcg gaa     624
Arg Arg Leu Leu Glu Leu Arg Gln Ile Pro Leu His Thr Ile Ala Glu
            195                 200                 205 aaa tgt ggc tat agc agt aca tcg tac ttt ata aac aca ttt cga caa     672
Lys Cys Gly Tyr Ser Ser Thr Ser Tyr Phe Ile Asn Thr Phe Arg Gln
            210                 215                 220 tat tat ggt gta acg cca cat cag ttt gcg caa cat tcg cca ggt acc     720
Tyr Tyr Gly Val Thr Pro His Gln Phe Ala Gln His Ser Pro Gly Thr
225                 230                 235                 240 ttt tcc tga                                                         729
Phe Ser

<210> SEQ ID NO 25
<211> LENGTH: 242
<212> TYPE: PRT
<213> ORGANISM: Escherichia coli

<400> SEQUENCE: 25

Met Thr His Val Cys Ser Val Ile Leu Ile Arg Arg Ser Phe Asp Ile
1               5                   10                  15

Tyr His Glu Gln Gln Lys Ile Ser Leu His Asn Glu Ser Ile Leu Leu
            20                  25                  30

Leu Glu Lys Asn Leu Ala Asp Asp Phe Ala Phe Cys Ser Pro Asp Thr
        35                  40                  45

Arg Arg Leu Asp Ile Asp Glu Leu Thr Val Cys His Tyr Leu Gln Asn
    50                  55                  60

Ile Arg Gln Leu Pro Arg Asn Leu Gly Leu His Ser Lys Asp Arg Leu
65                  70                  75                  80

Leu Ile Asn Gln Ser Pro Pro Met Pro Leu Val Thr Ala Ile Phe Asp
                85                  90                  95

Ser Phe Asn Glu Ser Gly Val Asn Ser Pro Ile Leu Ser Asn Met Leu
            100                 105                 110

Tyr Leu Ser Cys Leu Ser Met Phe Ser His Lys Glu Leu Ile Pro
        115                 120                 125

Leu Leu Phe Asn Ser Ile Ser Thr Val Ser Gly Lys Val Glu Arg Leu
    130                 135                 140

Ile Ser Phe Asp Ile Ala Lys Arg Trp Tyr Leu Arg Asp Ile Ala Glu
145                 150                 155                 160

Arg Met Tyr Thr Ser Glu Ser Leu Ile Lys Lys Leu Gln Asp Glu
                165                 170                 175

Asn Thr Cys Phe Ser Lys Ile Leu Leu Ala Ser Arg Met Ser Met Ala
            180                 185                 190

Arg Arg Leu Leu Glu Leu Arg Gln Ile Pro Leu His Thr Ile Ala Glu
        195                 200                 205

Lys Cys Gly Tyr Ser Ser Thr Ser Tyr Phe Ile Asn Thr Phe Arg Gln
    210                 215                 220

Tyr Tyr Gly Val Thr Pro His Gln Phe Ala Gln His Ser Pro Gly Thr
225                 230                 235                 240

Phe Ser
```

METHOD FOR PRODUCTION OF L-AMINO ACID

This application is a continuation of PCT/JP2007/068386, filed Sep. 21, 2007, which claims priority under 35 U.S.C. §119 to Japanese Patent Application No. 2006-276657, filed on Oct. 10, 2006, which are incorporated in their entireties by reference. The Sequence Listing in electronic format filed herewith is also hereby incorporated by reference in its entirety (File Name: US-389_Seq_List; File Size: 78 KB; Date Created: Apr. 9, 2009).

BACKGROUND OF THE INVENTION

1. Field of the Invention

The present invention relates to a method for producing an L-amino acid using a bacterium, and more particularly, to a method for producing an L-amino acid such as L-lysine, L-threonine, and L-tryptophan. L-lysine, L-threonine, and L-tryptophan are industrially useful as additives for animal feeds, components of health foods, amino acid infusions, and the like.

2. Brief Description of the Related Art

As methods for producing a target substance such as an L-amino acid by a fermentation method using a bacterium, there are known a method using a wild-type bacterium (wild-type strain), a method using an auxotrophic strain induced from a wild-type strain, a method using a metabolic control mutant induced from a wild-type strain as various drug-resistant mutants, and a method using a strain having properties of both the auxotrophic strain and the metabolic control mutant.

In recent years, fermentative production of a target substance is performed using a recombinant DNA technology. For example, improvement of L-amino acid productivity of a bacterium has been achieved by enhancing the expression of a gene encoding an L-amino acid biosynthetic enzyme (U.S. Pat. No. 5,168,056 and U.S. Pat. No. 5,776,736) or by enhancing the influx of a carbon source into an L-amino acid biosynthetic system (U.S. Pat. No. 5,906,925).

Glutamate decarboxylase (GAD) from *Escherichia coli* is an enzyme that produces γ-aminobutyric acid (GABA) from L-glutamic acid by decarboxylation reaction (Methods Enzymol. 1985. 113: 11-16. Fonda, M. L. L-Glutamate decarboxylase from bacteria.), and is known to play an important role in the resistance to an acid (J. Bacteriol. 1999. 181(11): 3525-3535. Castanie-Cornet, M. P., Penfound, T. A., Smith, D., Elliott, J. F., and Foster, J. W. Control of acid resistance in *Escherichia coli*.). Two kinds of GADs have been discovered in *Escherichia coli*, and one is encoded by gadA gene, and the other is encoded by gadB gene (J. Bacteriol. 1992. 174(18): 5820-5826. Smith, D. K., Kassam, T., Singh, B., and Elliott, J. F. *Escherichia coli* has two homologous glutamate decarboxylase genes that map to distinct loci.).

Meanwhile, the gadC gene is located downstream of gadB gene and forms an operon with the gadB gene, and is presumed to encode a glutamic acid/GABA antiporter (J. Bacteriol. 1996. 178(13): 3978-3981. Hersh, B. M., Farooq, F. T., Barstad, D. N., Blankenhorn, D. L., and Slonczewski, J. L. A glutamate-dependent acid resistance gene in *Escherichia coli*.). It has been disclosed that elimination of gadB is effective for production of an L-amino acid such as L-glutamic acid, L-proline, or L-leucine (RU Patent 2,264,457). However, there have been no reports of the production of an L-amino acid using a bacterium modified to enhance genes encoding GAD (gadA and gadB) or a gene encoding a transporter of GABA (gadC).

SUMMARY OF THE INVENTION

An aspect of the present invention is to provide a bacterium of the Enterobacteriaceae family that effectively produces an L-amino acid selected from the group consisting of L-lysine, L-threonine, and L-tryptophan, and to provide a method of effectively producing the L-amino acids using the bacterium.

The inventors of the present invention have made intensive studies to solve the above-mentioned objects. As a result, they have found that productivity of L-lysine, L-threonine, and L-tryptophan can be improved by modifying a bacterium to enhance the expression of gadA and gadB genes each encoding glutamate decarboxylase, and in an exemplary embodiment, by modifying a bacterium to further enhance the expression of gadC gene encoding glutamic acid/GABA antiporter.

It is an aspect of the invention to provide a method for producing an L-amino acid selected from the group consisting of L-lysine, L-threonine, and L-tryptophan, the method comprising cultivating an L-amino acid producing bacterium of the Enterobacteriaceae family in a medium; and collecting the L-amino acid from the medium, wherein the bacterium is modified to enhance glutamate decarboxylase activity.

It is another aspect of the invention to provide the method as described above, wherein the glutamate decarboxylase activity is enhanced by increasing the expression of a gene selected from the group consisting of the gadA gene and the gadB gene.

It is another aspect of the invention to provide the method as described above, wherein the gadA gene is a DNA selected from the group consisting of:

(a) a DNA comprising the nucleotide sequence of SEQ ID NO: 1; and (b) a DNA that hybridizes with a nucleotide sequence complementary to SEQ ID NO: 1, or a probe prepared from the nucleotide sequence, under stringent conditions, and encodes a protein that has glutamate decarboxylase activity.

It is another aspect of the invention to provide the method as described above, wherein the gadA gene encodes a protein selected from the group consisting of:

(A) a protein comprising the amino acid sequence of SEQ ID NO: 2; and (B) a protein comprising the amino acid sequence of SEQ ID NO: 2 but which includes one or more substitutions, deletions, insertions, additions, or inversions of one or several amino acids and the protein has glutamate decarboxylase activity.

It is another aspect of the invention to provide the method as described above, wherein the gadB gene is a DNA selected from the group consisting of:

(c) a DNA comprising the nucleotide sequence of SEQ ID NO: 3; and (d) a DNA that hybridizes with a nucleotide sequence complementary to SEQ ID NO: 3, or a probe prepared from the nucleotide sequence, under stringent conditions, and encodes a protein that has glutamate decarboxylase activity.

It is another aspect of the invention to provide the method as described above, wherein the gadB gene encodes a protein selected from the group consisting of:

(C) a protein comprising the amino acid sequence of SEQ ID NO: 4; and (D) a protein comprising the amino acid sequence of SEQ ID NO: 4 but which includes one or more substitutions, deletions, insertions, additions, or inversions of one or several amino acids and the protein has glutamate decarboxylase activity.

It is another aspect of the invention to provide the method as described above, wherein said bacterium is further modified to enhance glutamic acid/GABA antiporter activity.

It is another aspect of the invention to provide the method as described above, wherein glutamic acid/GABA antiporter activity is enhanced by increasing the expression of gadC gene.

It is another aspect of the invention to provide the method as described above, wherein the gadC gene is a DNA selected from the group consisting of:

(e) a DNA comprising the nucleotide sequence of SEQ ID NO: 5; and (f) a DNA that hybridizes with a nucleotide sequence complementary to SEQ ID NO: 5, or a probe prepared from the nucleotide sequence, under stringent conditions, and encodes a protein that has glutamic acid/GABA antiporter activity.

It is another aspect of the invention to provide the method as described above, wherein the gadC gene encodes a protein selected from the group consisting of:

(E) a protein comprising the amino acid sequence of SEQ ID NO: 6; and (F) a protein comprising the amino acid sequence of SEQ ID NO: 6 but which includes one or more substitutions, deletions, insertions, additions, or inversions of one or several amino acids and the protein has glutamic acid/GABA antiporter activity.

It is another aspect of the invention to provide the method as described above, wherein expression of the genes is increased by increasing the copy number of each of the genes, or modifying expression regulatory sequences of the genes.

It is another aspect of the invention to provide the method as described above, wherein said bacterium belongs to a genus selected from the group consisting of *Escherichia, Enterobacter, Pantoea, Klebsiella,* and *Serratia*.

DESCRIPTION OF THE PREFERRED EMBODIMENTS

Hereinafter, the present invention will be described in detail.

<1> Bacterium of the Present Invention

Exemplary bacteria of the present invention include a bacterium of the Enterobacteriaceae family that has an ability to produce an L-amino acid and is modified to enhance glutamate decarboxylase activity. The L-amino acid may be L-lysine, L-threonine, and L-tryptophan.

The term "ability to produce an L-amino acid" refers to an ability to produce and accumulate an L-amino acid at a level that is high enough to be collected from a medium or bacterial cells when a bacterium is cultured in the medium. The bacterium can have an ability to produce one of L-lysine, L-threonine, and L-tryptophan, or can have an ability to produce two or three of them. The bacterium having an ability to produce the L-amino acid can be one that originally has an ability to produce the L-amino acid, or one obtained by modifying any one of the bacteria mentioned below so as to have an ability to produce the L-amino acid by using a mutation method or a recombinant DNA technology.

Meanwhile, the phrase "expression of a gene is enhanced" refers to enhancement of a transcription and/or translation level of a gene.

<1-1> Imparting L-Amino Acid-Producing Ability

Hereinafter, methods of imparting an L-amino acid-producing ability will be described, as well as examples of bacteria to which an L-amino acid-producing ability have been imparted. However, the bacterium is not limited thereto, as long as it has an L-amino acid-producing ability.

Bacteria to be used can include, but are not limited to, bacteria belonging to the Enterobacteriaceae family such as those belonging to the genus *Escherichia, Enterobacter, Pantoea, Klebsiella, Serratia, Erwinia, Salmonella,* or *Morganella*, and which are able to produce L-amino acid. Specifically, bacteria belonging to the Enterobacteriaceae family according to the classification shown in NCBI (National Center for Biotechnology Information) database (www.ncbi.nlm.nih.gov/Taxonomy/Browser/wwwtax.cgi?id=91347) can be used. Among them, bacteria belonging to the genus *Escherichia, Enterobacter,* or *Pantoea* can be preferably used as the parent strain which is used for the modification.

*Escherichia* bacteria which can be used as the parent strain from which to derive the bacterium include, but are not limited to, the *Escherichia* bacteria reported in Neidhardt et al. ((Backmann, B. J. 1996. Derivations and Genotypes of some mutant derivatives of *Escherichia coli* K-12, p. 2460-2488. Table 1. In F. D. Neidhardt (ed.), *Escherichia coli* and *Salmonella* Cellular and Molecular Biology/Second Edition, American Society for Microbiology Press, Washington, D.C.), such as *Escherichia coli*. Specific examples of *Escherichia coli* include the *Escherichia coli* W3110 strain (ATCC No. 27325), and the MG1655 strain (ATCC No. 47076), both of which are derived from a wild-type (prototype) *Escherichia coli* K12 strain.

These strains are available from the American Type Culture Collection (ATCC) (Address: P.O. Box 1549, Manassas, Va. 20108, 1, United States of America). That is, each strain is given a unique registration number which is listed in the catalogue of the ATCC (www.atcc.org/). Strains can be ordered using this registration number.

Examples of *Enterobacter* bacteria include *Enterobacter agglomerans* and *Enterobacter aerogenes*, and an example of *Pantoea* bacteria is *Pantoea ananatis*. Recently, *Enterobacter agglomerans* was reclassified in some cases as *Pantoea agglomerans, Pantoea ananatis, Pantoea stewartii*, or the like, based on an analysis of the nucleotide sequence of 16S rRNA. Therefore, bacteria in accordance with the presently disclosed subject matter can belong to either the genus *Enterobacter* or the genus *Pantoea*, as long as they are classified in the Enterobacteriaceae family. When *Pantoea ananatis* is bred using genetic engineering techniques, *Pantoea ananatis* AJ13355 strain (FERM BP-6614), AJ13356 strain (FERM BP-6615), AJ13601 strain (FERM BP-7207), and derivatives thereof can be used. These strains were identified and deposited as *Enterobacter agglomerans* when they were isolated, but as described above, these strains have been reclassified as *Pantoea ananatis* based on an analysis of the nucleotide sequence of 16S rRNA.

Examples of methods of imparting or enhancing an ability to produce an L-amino acid selected from L-lysine, L-threonine and L-tryptophan to bacteria belonging to the Enterobacteriaceae family are described below.

In order to impart the L-amino acid-producing ability, methods may be used which are used in conventional breeding of *Escherichia* bacteria or the like, such as by acquiring nutrient-auxotrophic mutant strains, analogue resistant strains, or metabolic regulation mutant strains, or by creating recombinant strains having enhanced expression of L-amino acid biosynthetic enzymes (Amino Acid Fermentation, Japan Scientific Societies Press, first edition publication: May 30, 1986, p. 77 to 100). According to the presently disclosed subject matter, properties such as nutrient-auxotrophy, analogue-resistance, and metabolic regulation mutation can be imparted alone or in combination for imparting the L-amino acid-producing ability. Furthermore, expression of one or more L-amino acid biosynthetic enzymes can be enhanced. Furthermore, imparting of such properties as nutrient-auxotrophy, analogue-resistance, and metabolic regulation mutation can be combined with enhancing the expression of the L-amino acid biosynthetic enzymes.

Nutrient-auxotrophic mutant strains, L-amino acid-analogue resistant strains, and metabolic regulation mutant strains that have an L-amino acid-producing ability can be obtained as follows. A parent strain or a wild-type strain is subjected to a typical mutation treatment, such as irradiation with X-rays or ultraviolet rays, or by treating with a mutagen, including N-methyl-N'-nitro-N-nitrosoguanidine (NTG) and ethylmethanesulfonate (EMS), followed by selection of the strains that exhibit nutrient-auxotrophy, analogue-resistance, or a metabolic regulation mutation and have an L-amino acid-producing ability.

Hereinafter, L-lysine-producing bacteria and methods of constructing L-lysine-producing bacteria are exemplified.

Examples of parent strains which have L-lysine-producing ability can include bacteria resistant to an L-lysine analogue and bacteria having a metabolic regulation mutation. Examples of an L-lysine analogue can include oxalysine, lysinehydroxamate, S-(2-aminoethyl)-L-cysteine (AEC), γ-methyllysine, and α-chlorocaprolactam. L-lysine analogue resistant strains can be obtained by treating a bacterium of the Enterobacteriaceae family with conventional mutagenesis. Specific examples of an L-lysine analogue resistant strain and metabolic regulation mutant strain having an L-lysine-producing ability can include Escherichia coli AJ11442 strain (FERM BP-1543, NRRL B-12185; JP 56-18596 A and U.S. Pat. No. 4,346,170) and Escherichia coli VL611 strain (JP 2000-189180 A). WC196 strain (WO 96/17930) can be used as an L-lysine producing strain of Escherichia coli. WC196 strain has been obtained by imparting AEC-resistance to W3110 strain which was derived from Escherichia coli K-12 strain. The WC196 strain was named Escherichia coli AJ13069 strain and deposited at the National Institute of Bioscience and Human-Technology, Agency of Industrial Science and Technology (currently, International Patent Organism Depositary, National Institute of Advanced Industrial Science and Technology, Central 6, 1-1-1 Higashi, Tsukuba, Ibaraki 305-8566, Japan) on Dec. 6, 1994 and given an accession number of FERM P-14690, and the deposit was then converted to an international deposit under the provisions of Budapest Treaty on Sep. 29, 1995 and given an accession number of FERM BP-5252.

L-lysine producing bacteria can be constructed by enhancing an activity of an L-lysine biosynthetic enzyme. The activity of an L-lysine biosynthetic enzyme can be enhanced by increasing the copy number of a gene encoding the L-lysine biosynthetic enzyme or by modifying an expression regulatory sequence of a gene encoding the enzyme. Increasing the copy number or modifying the expression regulatory sequence can be performed in the same way as the gadA, gadB, and gadC genes described below.

Examples of a gene encoding L-lysine biosynthetic enzyme can include, but are not limited to, those encoding an enzyme in the diaminopimelate pathway such as dihydrodipicolinate synthase gene (dapA: hereinafter, the words in parentheses represent the gene names), aspartokinase gene (lysC), dihydrodipicolinate reductase gene (dapB), diaminopimelate decarboxylase gene (lysA), diaminopimelate dehydrogenase gene (ddh) (WO96/40934), phosphoenolpyruvate carboxylase gene (ppc) (JP 60-87788 A), aspartate aminotransferase gene (aspC) (JP 06-102028 B), diaminopimelate epimerase gene (dapF) (JP 2003-135066), and aspartate semialdehyde dehydrogenase gene (asd) (WO 00/61723); and genes encoding enzymes in the aminoadipic acid pathway such as homoaconitate hydratase (JP 2000-157276 A). The parenthetical descriptions above represent the gene names.

It is known that wild-type DDPS derived from Escherichia coli is regulated by feedback inhibition by L-lysine, while wild-type aspartokinase derived from Escherichia coli is regulated by suppression and feedback inhibition by L-lysine. Therefore, when using dapA and lysC, mutated forms of these genes can be used so that the enzymes encoded by the genes are not subject to feedback inhibition.

An example of a DNA encoding mutant DDPS desensitized to feedback inhibition by L-lysine can include a DNA encoding a DDPS which has an amino acid sequence in which the histidine at position 118 is replaced by tyrosine. Meanwhile, an example of a DNA encoding mutant aspartokinase III (AKIII) desensitized to feedback inhibition by L-lysine can include a DNA encoding an AKIII having an amino acid sequence in which the threonine at position 352, the glycine at position 323, and the methionine at position 318 are replaced by isoleucine, asparagine and isoleucine, respectively (U.S. Pat. No. 5,661,012 and U.S. Pat. No. 6,040,160). Such mutant DNAs can be obtained by a site-specific mutation using PCR or the like.

Wide host-range plasmids RSFD80, pCAB1, and pCABD2 are known to contain a mutant dapA gene encoding a mutant DDPS and a mutant lysC gene encoding a mutant AKIII (U.S. Pat. No. 6,040,160). Escherichia coli JM109 strain transformed with RSFD80 was named AJ12396 (U.S. Pat. No. 6,040,160), and the strain was deposited at the National Institute of Bioscience and Human-Technology, Agency of Industrial Science and Technology, Ministry of International Trade and Industry (currently, International Patent Organism Depositary, National Institute of Advanced Industrial Science and Technology) on Oct. 28, 1993 and given an accession number of FERM P-13936, and the deposit was then converted to an international deposit under the provisions of Budapest Treaty on Nov. 1, 1994 and given an accession number of FERM BP-4859. RSFD80 can be obtained from AJ12396 strain by a conventional method.

Furthermore, in the L-amino acid producing bacterium, an activity of an enzyme that catalyzes a reaction which branches off from the L-amino acid biosynthetic pathway and produces another compound can be decreased or can be made deficient. Examples of such an enzyme for L-lysine production can include homoserine dehydrogenase, lysine decarboxylase (cadA, ldcC), and malic enzyme, and strains in which activities of such enzymes are decreased or deficient are described in WO 95/23864, WO 96/17930, WO 2005/010175, and the like.

A decrease or elimination of the lysine decarboxylase activity can be achieved by decreasing the expression of both of the cadA gene and ldcC gene, which encode lysine decarboxylase. Expression of these genes can be decreased by the method shown in Example 2 below.

Examples of cadA gene can include a DNA which includes the nucleotide sequence of SEQ ID NO: 12 and a DNA that hybridizes with a nucleotide sequence complementary to SEQ ID NO: 12 or a probe prepared from the nucleotide sequence under stringent conditions, and encodes a protein that has lysine decarboxylase activity.

Examples of ldcC gene can include a DNA which includes the nucleotide sequence of SEQ ID NO: 14 and a DNA that hybridizes with a nucleotide sequence complementary to SEQ ID NO: 14 or a probe prepared from the nucleotide sequence under stringent conditions, and encodes a protein that has lysine decarboxylase activity.

The term "stringent conditions" are as described below.

Activities of these enzymes can be decreased or eliminated by introducing a mutation to the genes encoding the enzymes on the chromosome using a known mutation treatment, to thereby decrease or eliminate the activities of the enzymes in a cell. For example, decreasing or eliminating the activities of the enzymes can be attained by disrupting the genes encoding the enzymes on the chromosome by gene recombination or by modifying an expression regulatory sequence such as a promoter or Shine-Dalgarno (SD) sequence. In addition, this can also be attained by introducing an amino acid substitution (missense mutation) to the region encoding the enzymes on the chromosome, introducing a stop codon (nonsense mutation), introducing a frameshift mutation that adds or deletes one or two nucleotides, or deleting part of the gene (Journal of biological Chemistry 272: 8611-8617 (1997). Meanwhile, the activities of the enzymes can also be decreased or eliminated by constructing a mutant gene encoding a mutant enzyme which has a deletion in the coding region, and then replacing the normal gene on the chromosome with the mutant gene by homologous recombination, or introducing the mutant gene using a transposon or an IS factor.

For example, the following gene recombination method can be used to introduce a mutation that decreases or eliminates the activities of the above-mentioned enzymes. A mutant gene is prepared by modifying a partial sequence of a target gene so that it does not encode an enzyme that can function normally. Then, a bacterium belonging to the Enterobacteriaceae family is transformed with a DNA containing the mutant gene to cause recombination of a gene on the bacterial chromosome with the mutant gene, thereby substituting the target gene on the chromosome with the mutant gene. Examples of this type of gene substitution using homologous recombination can include the method using a linear DNA called "Red-driven integration" (Datsenko, K. A, and Wanner, B. L. Proc. Natl. Acad. Sci. USA. 97: 6640-6645 (2000), a combination of Red-driven integration and a cleavage system derived from λ phage (Cho, E. H., Gumport, R. I., Gardner, J. F. J. Bacteriol. 184: 5200-5203 (2002)) (WO 2005/010175), a method using a plasmid containing a temperature-sensitive replication origin (Datsenko, K. A, and Wanner, B. L. Proc. Natl. Acad. Sci. USA. 97: 6640-6645 (2000); U.S. Pat. No. 6,303,383; JP 05-007491 A), and the like. Meanwhile, a site-specific mutation by gene substitution using homologous recombination can also be performed by using a plasmid which is not able to replicate in a host cell.

Hereinafter, methods of breeding L-tryptophan producing strains and L-threonine producing strains will be described.

Examples of L-tryptophan-producing bacteria which can be used in accordance with the disclosed subject matter can include strains in which one or more activities of the enzymes selected from anthranilate synthase, phosphoglycerate dehydrogenase, and tryptophan synthase are enhanced. The anthranilate synthase and phosphoglycerate dehydrogenase are both subject to feedback inhibition by L-tryptophan and L-serine, so a mutation which results in resistance to the feedback inhibition can be introduced into these enzymes. Specifically, a bacterium belonging to the Enterobacteriaceae family and harboring the feedback resistant enzymes can be obtained by mutating the anthranilate synthase and phosphoglycerate dehydrogenase so as to be resistant to the feedback inhibition and introducing the mutant enzymes into the bacterium. Specific examples of strains having such a mutation can include a strain obtained by introducing the plasmid pGH5 (WO 94/08031) which contains a serA gene which has been mutated so that it encodes feedback-desensitized phosphoglycerate dehydrogenase into E. coli SV164 strain. SV164 strain was obtained by introducing a mutant gene encoding feedback-desensitized anthranilate synthase into E. coli KB862 (DSM7196) strain which is deficient in trpE (WO94/08031).

Examples of L-tryptophan-producing bacteria also can include strains introduced with a recombinant DNA which includes the tryptophan operon. Specifically, an Escherichia coli introduced with a tryptophan operon which contains a gene encoding desensitized anthranilate synthase (JP 57-71397 A, JP 62-244382 A, U.S. Pat. No. 4,371,614). Moreover, L-tryptophan-producing ability can be imparted by enhancing expression of a gene which encodes tryptophan synthase, among tryptophan operons (trpBA). The tryptophan synthase includes α and β subunits which are encoded by trpA and trpB, respectively.

A strain which is deficient in trpR (a repressor of tryptophan operon) and a strain having a mutation in trpR are possible examples of an L-tryptophan-producing strain (U.S. Pat. No. 4,371,614 and WO2005/056776).

Strains in which malate synthase-isocitrate lyase-isocitrate dehydrogenasekinase/phosphatase operon (ace operon) is constitutively expressed or expression of the operon is enhanced are further examples of an L-tryptophan-producing strain. In an exemplary embodiment of the presently disclosed subject matter, the promoter of the ace operon is not suppressed by its repressor (iclR) or the suppression by iclR is released. Such strains can be obtained by disrupting the iclR gene or by modifying the expression regulatory sequence of the ace operon. A strain in which the expression of the ace operon is enhanced can be obtained by connecting a DNA which includes the ace operon to a strong promoter, and introducing it into cells by a plasmid or homologous recombination or by transferring it so that multiple copies of the DNAs are integrated into the chromosomal DNA. The ace operon includes aceB, aceA and aceK.

Examples of the L-tryptophan-producing bacteria also can include E. coli AGX17 (pGX44) strain (NRRL B-12263) which is auxotrophic for L-phenylalanine and L-tyrosine, and AGX6(pGX50)aroP strain (NRRL B-12264) which harbors plasmid pGX50 comprising tryptophan operon (U.S. Pat. No. 4,371,614). These strains are available from Agricultural Research Service Culture Collection, National Center for Agricultural Utilization Research (Peoria, Ill. 61604, USA).

L-tryptophan, L-phenylalanine and L-tyrosine are aromatic amino acids and have common synthetic pathways. Examples of aromatic amino acid synthetic enzymes can include 3-deoxyarabino-heptulosonic acid 7-phosphate synthase (aroG), 3-dehydrokinate synthase (aroB), shikimic acid dehydratase, shikimic acid kinase (aroL), 5-enol-pyruvylshikimic acid 3-phosphate synthase (aroA), and chorismic acid synthase (aroC) (EP763127A). Thus, an ability to produce these aromatic amino acids can be enhanced by increasing the copy number of a gene encoding one or more of these enzymes with a plasmid or on a chromosome. Furthermore, these genes are regulated by tyrosine repressor (tyrR) and therefore the ability to produce these aromatic amino acids can be enhanced by disrupting the tyrR gene (EP763127A).

3-deoxyarabino-heptulosonic acid 7-phosphate synthase (aroF and aroG) is sensitive to feedback inhibition by aromatic amino acids, so the enzyme can be modified so as to be resistant to the feedback inhibition. For example, aromatic amino acids can be efficiently produced by introducing into the host a mutant aroF gene which encodes a mutant enzyme in which aspartic acid residue at position 147 and serine residue at position 181 can be replaced with another amino acid residue and a mutant aroG gene encoding a mutant enzyme in which one of aspartic acid residue at position 146, methionine residue at position 147, proline residue at position 150, alanine residue at position 202 can be replaced with another amino acid residue or both the methionine residue at position 157 and alanine residue at position 219 can be replaced with another amino acid residue (EP0488424).

Examples of L-threonine-producing bacteria which can be used in accordance with the presently disclosed subject matter can include, but are not limited to, bacteria belonging to the Enterobacteriaceae family in which activities of L-threonine biosynthetic enzymes are enhanced. Examples of genes encoding L-threonine synthetic enzymes can include aspartokinase III gene (lysC), aspartate semialdehyde dehydrogenase (asd), and aspartokinase I gene (thrA), homoserine kinase gene (thrB), and threonine synthase gene (thrC) which are encoded by threonine operon. Two or more of the genes can be introduced. The genes encoding L-threonine synthetic enzymes can be introduced into a bacterium belonging to the Enterobacteriaceae family in which threonine decomposition is decreased. An example of an E. coli strain in which threonine decomposition is decreased includes TDH6 strain which is deficient in threonine dehydrogenase activity (JP2001-346578A).

Activities of L-threonine biosynthetic enzymes are inhibited by the end product L-threonine, so L-threonine biosynthetic enzymes can be modified in this particular example so as to be desensitized to feedback inhibition by L-threonine for constructing L-threonine producing strains. The above-described thrA gene, thrB gene and thrC gene constitute a threonine operon whose promoter has an attenuator structure. Since the expression of the threonine operon is inhibited by isoleucine and threonine in the culture medium and also inhibited by attenuation, the threonine operon can be modified in this particular example by removing the leader sequence or attenuator in the attenuation region (Lynn, S. P., Burton, W. S., Donohue, T. J., Gould, R. M., Gumport, R. I., and Gardner, J. F. J. Mol. Biol. 194:59-69 (1987); WO02/26993; WO2005/049808).

The native promoter of the threonine operon can be replaced by a non-native promoter (WO98/04715), or the threonine operon can be connected to the repressor and promoter of λ-phage so that expression of the threonine synthetic genes can be controlled by the repressor and promoter of λ-phage (EP0593792).

Furthermore, mutant Escherichia bacteria that are desensitized to feedback inhibition by L-threonine can be obtained by screening for strains resistant to α-amino β-hydroxy isovaleric acid (AHV).

In one example, it is possible to increase the copy number of the thereonine operon that is modified so as to be desensitized to feedback inhibition by L-threonine in a host bacterium or increase the expression of the modified operon by connecting it to a potent promoter. The copy number can be increased by using, in addition to a plasmid, a transposon or Mu-phage so that the operon is transferred onto a chromosome of a host bacterium.

The gene encoding aspartokinase (lysC) can be modified in one example to be desensitized to feedback inhibition by L-lysine. Such a modified lysC gene can be obtained by the method described in U.S. Pat. No. 5,932,453.

L-threonine producing bacterium can also be obtained by enhancing the expression of genes involved in the glycolytic pathway, TCA cycle, or respiratory chain, or genes that regulate the expression of these genes, or genes involved in sugar uptake. Examples of these genes that are effective for L-threonine production can include transhydrogenase gene (pntAB) (EP733712B), phosphoenolpyruvate carboxylase gene (ppc) (WO95/06114), phosphoenolpyruvate synthase gene (pps) (EP877090B), pyruvate carboxylase gene derived from coryneform bacterium or Bacillus bacterium (WO99/18228, EP1092776A).

L-threonine producing bacterium can also be obtained by enhancing the expression of a gene that imparts L-threonine resistance and/or a gene that imparts L-homoserine resistance, or by imparting L-threonine resistance and/or L-homoserine resistance to a host bacterium. Examples of the genes that impart L-threonine resistance include the rhtA gene (Res. Microbiol. 154:123-135 (2003)), rhtB gene (EP0994190A), rhtC gene (EP1013765A), yfiK gene, and yeaS gene (EP1016710A). Methods for imparting L-threonine resistance to a host bacterium are described in EP0994190A or WO90/04636.

E. coli VKPM B-3996 (U.S. Pat. No. 5,175,107) is also exemplified as an L-threonine-producing bacterium. The strain B-3996 was deposited on Apr. 7, 1987 in the the Russian National Collection of Industrial Microorganisms (VKPM), GNII Genetika, (Russia, 117545 Moscow 1, Dorozhny proezd. 1) under the accession number VKPM B-3996. The strain B-3996 contains the plasmid pVIC40 (WO90/04636) which was obtained by inserting threonine biosynthetic genes (threonine operon: thrABC) into a wide host range plasmid vector pAYC32 containing a streptomycin resistance marker (Chistorerdov, A. Y., and Tsygankov, Y. D. Plasmid, 16, 161-167 (1986)). In pVIC40, the threonine operon contains a mutant thrA gene which encodes aspartokinase homoserine dehydrogenase I which is substantially desensitized to feedback inhibition by threonine.

E. coli VKPM B-5318 (EP 0593792B) is also exemplified as another possible L-threonine-producing bacterium. The VKPM B-5318 strain was deposited in the Russian National Collection of Industrial Microorganisms (VKPM) (Russia, 117545 Moscow 1, Dorozhny proezd. 1) on May 3, 1990 under accession number of VKPM B-5318. The VKPM B-5318 strain is prototrophic with regard to L-isoleucine, and harbors a plasmid DNA which contains the threonine operon encoding the threonine biosynthesis enzyme located downstream of the C1 temperature-sensitive repressor, PR-promoter and N-terminal of Cro protein derived from λphage so that the expression of the threonine operon is regulated by the promoter and repressor derived from λ phage.

Expression of genes other than the L-amino acid biosynthetic genes can also be enhanced in the L-amino acid producing bacterium to be used in accordance with the presently disclosed subject matter, and examples of such genes can include those encoding enzymes involved in sugar uptake, sugar metabolism (glycolytic pathway), and energy metabolism.

Genes involved in sugar metabolism include genes encoding enzymes in the glycolytic pathway or enzymes involved in sugar uptake. Examples thereof include the glucose-6-phosphate isomerase gene (pgi; WO 01/02542), phosphoenolpyruvate synthase gene (pps; EP 877090 A), phosphoglucomutase gene (pgm; WO 03/04598), fructose bisphosphate aldolase gene (fba; WO 03/04664), pyruvate kinase gene (pykF; WO 03/008609), transaldolase gene (talB; WO 03/008611), fumarase gene (fum; WO 01/02545), phosphoenolpyruvate synthase gene (pps; EP 877090 A), non-PTS sucrose uptake gene (csc; EP 149911 A), and sucrose-assimilating gene (scrAB operon; WO 90/04636).

Examples of genes encoding enzymes involved in energy metabolism can include transhydrogenase gene (pntAB; U.S. Pat. No. 5,830,716) and cytochromoe bo type oxidase gene (cyoB; EP 1070376).

The bacterium in accordance with the presently disclosed subject matter can be obtained by modifying a bacterium having an ability to produce an L-amino acid such as L-lysine, L-threonine, and L-tryptophan as described above to enhance glutamate decarboxylase activity.

As described below, enhancement of glutamate decarboxylase activity can be achieved by enhancing the expression of a gene encoding glutamate decarboxylase. The expression can be enhanced by increasing expression of an endogenous gene by modification of an expression regulatory region such as a promoter; or increasing expression of an exogenous gene by introduction of a plasmid containing the gene or the like. In addition, these methods can be combined.

The term "glutamate decarboxylase activity" refers to an activity of glutamate decarboxylase (GAD) that irreversibly catalyzes the reaction to produce γ-aminobutyric acid (GABA) by decarboxylation at the α-position of L-glutamic acid (EC: 4.1.1.15), and the phrase "modified to enhance glutamate decarboxylase activity" includes when the number of glutamate decarboxylase molecules per cell increases and when the glutamate decarboxylase activity per molecule is improved as compared to a wild-type strain or an unmodified strain. The bacterium is preferably modified so that the glutamate decarboxylase activity is improved not less than 150% per bacterial cell, more preferably not less than 200%, furthermore preferably not less than 300% per bacterial cell as compared to a wild-type strain or an unmodified strain. In the present invention, examples of wild-type bacteria belonging to the Enterobacteriaceae family to be used as a control include *Escherichia coli* MG1655 strain (ATCC No. 47076), W3110 strain (ATCC No. 27325), and *Pantoea ananatis* AJ13335 strain (FERM BP-6615). The glutamate decarboxylase activity can be determined by, for example, the method described in Methods Enzymol. 1985, 113: 11-16.

The glutamate decarboxylase activity can be enhanced by increasing the expression of a gene encoding glutamate decarboxylase. *Escherichia coli* is known to have a gadA gene encoding GadA protein (SEQ ID NO: 2) and a gadB gene encoding GadB protein (SEQ ID NO: 4) as GAD. GadA and GadB are known to be isozymes having a very high homology (having 99% amino acid homology) (J. Bacteriol. 174. 5820 (1992)).

The increased expression of a gene encoding glutamate decarboxylase compared to a parent strain such as a wild-type or unmodified strain can be confirmed by comparing the mRNA level with that of a wild-type or unmodified strain. Examples of a method of confirming the expression can include Northern hybridization and RT-PCR (Molecular Cloning (Cold Spring Harbor Laboratory Press, Cold spring Harbor (USA), 2001)). The expression can be any level as long as it is increased as compared to a wild-type or unmodified strain, and for example, the level is preferably increased not less than 1.5-fold, and in another example not less than 2-fold, and in another example not less than 3-fold as compared to a wild-type or unmodified strain. Meanwhile, enhancement of glutamate decarboxylase activity can be confirmed by an increase in the level of a target protein as compared to a wild-type or unmodified strain, and the protein level can be detected by, for example, Western blotting using an antibody (Molecular Cloning (Cold Spring Harbor Laboratory Press, Cold Spring Harbor (USA), 2001)).

The bacterium of the Enterobacteriaceae family that can be used in the production method can be further modified to enhance glutamic acid/GABA antiporter activity in addition to the enhancement of glutamate decarboxylase activity.

The glutamic acid/GABA antiporter is known to be involved in acid resistance of cells grown in neutral pH at the time of addition of glutamic acid, and is presumed to play a role in maintaining the pH in cells in cooperation with GAD by simultaneously exporting intercellular glutamic acid and importing extracellular GABA (J. Bacteriol. 178, 3978 (1996)). *Escherichia coli* is known to have a gadC gene encoding GadC protein (SEQ ID NO: 6), which functions as a glutamic acid/GABA antiporter. The glutamic acid/GABA antiporter activity can be determined by, for example, the method described in J. Bacteriol. 178, 3978-3981 (1996).

Therefore, the "glutamate decarboxylase" in accordance with the presently disclosed subject matter can refer to GadA protein or GadB protein, and the "glutamic acid/GABA antiporter" refers to GadC protein.

As described in J. Bacteriol., 1996, 178(13): 3978-3981, gadB gene and gadC gene form an operon on the genome of *E. coli*, so the operon can be used to simultaneously enhance expression of gadB and gadC genes. Hereinafter, the operon including the gadB and gadC genes is referred to as the gadBC operon, in some cases.

The enhanced expression of genes encoding GadA, GadB, and GadC proteins (gadA, gadB, and gadC genes) as compared to a parent strain such as a wild-type or unmodified strain can be confirmed by comparing the mRNA level with that of a wild-type or unmodified strain. Examples of the method of confirming the expression include Northern hybridization and Reverse-Transcriptase PCR (RT-PCR) (Sambrook, J., and Russell, D. W., Molecular Cloning A Laboratory Manual/Third Edition. New York: Cold Spring Harbor Laboratory Press (2001)). The expression level can be any level as long as it is increased as compared to a wild-type or unmodified strain, and in one example, the level can be increased not less than 1.5-fold, in another example not less than 2-fold, and in another example not less than 3-fold as compared to a wild-type or unmodified strain.

Meanwhile, the enhanced expression can be confirmed by an increase in the level of a target protein as compared to a wild-type or unmodified strain, and the protein level may be detected by, for example, Western blotting using an antibody (Sambrook, J., and Russell, D. W., Molecular Cloning A Laboratory Manual/Third Edition. New York: Cold Spring Harbor Laboratory Press (2001)).

The gadA gene includes the gadA gene of, native to, or derived from an *Escherichia* bacterium, and a homologue thereof. Examples of the gadA gene of *Escherichia coli* can include a gene (SEQ ID NO: 1) that encodes a protein having the amino acid sequence of SEQ ID NO: 2 (GenBank Accession No. AAC76542 [GI: 1789934]).

The gadB gene includes the gadB gene of, native to, or derived from an *Escherichia* bacterium, and a homologue thereof. Examples of the gadB gene of *Escherichia coli* can include a gene (SEQ ID NO: 3) that encodes a protein having the amino acid sequence of SEQ ID NO: 4 (GenBank Accession No. AAC74566 [GI: 1787769]).

The homologues of gadA and gadB genes include genes that are derived from another microorganism, have high structural similarity to the gadA gene of an *Escherichia* bacterium, improve the ability to produce an L-amino acid selected from L-lysine, L-threonine, and L-tryptophan when they are introduced in a host, and encode a protein having glutamate decarboxylase activity. Examples of the homologues of gadA and gadB genes can include gadA genes of a *Shigella* bacterium, *Vibrio* bacterium, and the like registered in GenBank. In addition, the gadA gene can be obtained by cloning, based on homology to any of the above-mentioned genes, from a *Streptomyces* bacterium such as *Streptomyces coelicolor*, a *Mycobacterium* such as *Mycobacterium tuberculosis*, or lactic acid bacterium such as *Lactococcus* or *Lac-*

*tobacillus*. The homologues may be given different gene names as long as they have high homology to the gadA of an *Escherichia* bacterium. For example, the homologue of the gadA gene also can include a gene obtained by cloning using synthetic oligonucleotides of SEQ ID NOS: 8 and 9. Meanwhile, the homologue of gadB gene can include a gene obtained by cloning using synthetic oligonucleotides of SEQ ID NOS: 10 and 20.

Further, the homologues of the gadA and gadB genes can be obtained by selecting genes having high homologies from a known database based on the above-mentioned sequence information. The homologies of amino acid sequences and nucleotide sequences can be determined by using, for example, the algorithm BLAST (Proc. Natl. Acad. Sci. USA, 90, 5873 (1993)) or FASTA (Methods Enzymol., 183, 63 (1990)) created by Karlin and Altschul. Based on the algorithm BLAST, programs called BLASTN and BLASTX have been developed (www.ncbi.nlm.nih.gov).

The gadC gene in accordance with the presently disclosed subject matter can includes the gadC gene of, native to, or derived from an *Escherichia* bacterium, and a homologue thereof. Examples of the gadC gene of *Escherichia coli* can include a gene (SEQ ID NO: 5) that encodes a protein having the amino acid sequence of SEQ ID NO: 6 (GenBank Accession No. AAC74565 [GI: 1787768]).

As with the above-mentioned homologue of the gadA gene, the homologue of gadC gene refers to a gene that is derived from another microorganism, has high structural similarity to the gadC gene of an *Escherichia* bacterium, improves an ability to produce an L-amino acid selected from L-lysine, L-threonine, and L-tryptophan when it is introduced in a host, and encodes a protein having glutamic acid/GABA antiporter activity. The homologue of gadC gene can include a gene obtained by cloning using synthetic oligonucleotides of SEQ ID NOS: 11 and 21.

The gadA gene and gadB gene to be used in accordance with the presently disclosed subject matter are not limited to wild-type genes and can be mutant or artificially modified genes that encode a protein having the amino acid sequence of SEQ ID NO: 2 or 4 including substitutions, deletions, insertions, additions of one or several amino acids at one or a plurality of positions, as long as the function of the protein encoded by the genes, that is, glutamate dehydrogenase activity is maintained.

The gadC gene to be used is not limited to a wild-type gene and can be a mutant or artificially modified gene that encodes a protein having the amino acid sequence of SEQ ID NO: 6 including substitution, deletion, insertion, addition of one or several amino acids at one or a plurality of positions, as long as the function of the protein encoded by the gene, that is, glutamic acid/GABA antiporter activity is maintained.

In accordance with the presently disclosed subject matter, the term "one or several" specifically means 1 to 20, preferably 1 to 10, and more preferably 1 to 5, although this determination depends on the position in the protein's tertiary structure or the types of amino acid residues in the protein. The above-mentioned substitution by way of example can be a conservative substitution, which can include substitutions between aromatic amino acids such as substitution among Phe, Trp and Tyr, substitution between hydrophobic amino acids such as substitution among Leu, Ile and Val, substitution between polar amino acids such as substitution between Gln and Asn, substitution between basic amino acids such as substitution among Lys, Arg and His, substitution between acidic amino acids such as substitution between Asp and Glu, substitution between hydroxyl group-containing amino acids such as substitution between Ser and Thr. Examples of conservative substitutions can include substitution of Ser or Thr for Ala; substitution of Gln, His or Lys for Arg; substitution of Glu, Gln, Lys, His or Asp for Asn; substitution of Asn, Glu or Gln for Asp; substitution of Ser or Ala for Cys; substitution of Asn, Glu, Lys, His, Asp or Arg for Gln; substitution of Gly, Asn, Gln, Lys or Asp for Glu; substitution of Pro for Gly; substitution of Asn, Lys, Gln, Arg or Tyr for His; substitution of Leu, Met, Val or Phe for Ile; substitution of Ile, Met, Val or Phe for Leu; substitution of Asn, Glu, Gln, His or Arg for Lys; substitution of Ile, Leu, Val or Phe for Met; substitution of Trp, Tyr, Met, Ile or Leu for Phe; substitution of Thr or Ala for Ser; substitution of Ser or Ala for Thr; substitution of Phe or Tyr for Trp; substitution of His, Phe or Trp for Tyr; and substitution of Met, Ile or Leu for Val. Meanwhile, the above-mentioned amino acid substitution, deletion, insertion, addition or inversion can be a result of a naturally-occurring mutation (mutant or variant) due to an individual difference, a difference of species of a bacterium harboring the gadA gene, gadB gene or gadC gene. Such a homologue gene can be obtained by modifying the nucleotide sequence of SEQ ID NO: 1, 3 or 5 with site-specific mutagenesis so that the modified gene encodes a protein that has a substitution, deletion, insertion or addition of the amino acid residue at a specific position.

The gadA gene and gadB gene can include genes that encode amino acid sequences having homologies of not less than 80% in one example, not less than 90% in another example, not less than 95% in another example, and not less than 97% in another example, to the entire amino acid sequences of SEQ ID NO: 2 or 4, respectively, and encode a protein which can have glutamate dehydrogenase activity.

The gadC gene can include genes that encode amino acid sequences having homologies of not less than 80% in one example, not less than 90% in another example, not less than 95% in another example, and not less than 97% in another example, to the entire amino acid sequences of SEQ ID NO: 6, and encode a protein which can have glutamic acid/GABA antiporter activity.

The gadA gene, gadB gene and gadC gene can be modified so that the genes include codons which are easily translated into amino acids in a host cell. Furthermore, each of the gadA gene, gadB gene and gadC gene can encode a protein which has a deletion or addition at the amino terminal portion or carboxy terminal portion of the GadA protein, GadB gene and GadC protein as long as the glutamate dehydrogenase activity or the glutamic acid/GABA antiporter activity is maintained. The length of the amino acids to be deleted from the amino terminus or carboxy terminus or to be added at the amino terminus or carboxy terminus of the the GadA protein, GadB gene and GadC protein can be not more than 50 in one example, not more than 20 in another example, not more than 10 in another example, and not more than 5 in another example. Specifically, the GadA protein, GadB gene and GadC protein can have an amino acid sequence of SEQ ID NO: 2, 4 and 6 in which 5 to 50 amino acids are deleted from the amino terminus or carboxy terminus, or an amino acid sequence of SEQ ID NO: 2, 4 or 6 in which 5 to 50 amino acids are added to the amino terminus or carboxy terminus.

Homologues of the gadA gene, gadB gene and gadC gene can also be obtained by conventional mutagenesis techniques. Examples of the mutagenesis technique can include a method of treating the gadA gene, gadB gene, and gadC gene with hydroxylamine in vitro and a method of treating a bacterium such as *Escherichia* bacterium which harbors the gadA gene, gadB gene, and gadC gene with ultraviolet rays, or with a mutagen, including N-methyl-N'-nitro-N-nitrosoguanidine (NTG) and ethylmethanesulfonate (EMS).

Whether the obtained gene encodes a protein having glutamate dehydrogenase activity or glutamic acid/GABA antiporter activity can be confirmed by expressing the gene into a suitable host and evaluating that the host has been imparted with the glutamate dehydrogenase activity or the glutamic acid/GABA antiporter activity.

Meanwhile, the gadA gene, and gadB gene can hybridize with a complementary strand of the nucleotide sequence of SEQ ID NO: 1 or 3, or with a probe that can be prepared from the sequence, under stringent conditions and encodes a protein which has glutamate dehydrogenase activity. The gadC gene can hybridize with a complementary strand of the nucleotide sequence of SEQ ID NO: 5, or with a probe that can be prepared from the sequence under stringent conditions and encodes a protein which can have glutamic acid/GABA antiporter activity.

The term "stringent conditions" refers to conditions where a so-called specific hybrid is formed and a non-specific hybrid is not formed. It is difficult to clearly define the conditions by numerical value, but examples thereof include conditions where DNAs having high homology, in one example, at least 80%, in another example 90%, in another example 95%, and in another example 97%, homology hybridize with each other and DNAs having homology less than the value do not hybridize with each other; and specifically include washing condition typical of Southern hybridization, in one example, washing at 60° C., 1×SSC, 0.1% SDS, in another example, 60° C., 0.1×SSC, 0.1% SDS, and in another example, 68° C., 0.1×SSC, 0.1% SDS, once or preferably twice or three times.

As a probe, a partial sequence of the nucleotide sequence complementary to SEQ ID NO: 1, 3 or 5 can also be used. Such a probe can be prepared by PCR using oligonucleotides produced based on the nucleotide sequence of SEQ ID NO: 1, 3 or 5 as primers, and a DNA fragment containing the nucleotide sequence of SEQ ID NO: 1, 3 or 5 as a template. When a DNA fragment of a length of about 300 bp is used as the probe, the conditions of washing for the hybridization consist of, for example, 50° C., 2×SSC, and 0.1% SDS.

Expression of the above-mentioned gadA, gadB and gadC genes can be increased by, for example, increasing the copy number of the genes in a cell using a gene recombination technique. For example, a DNA fragment containing the gadA, gadB and gadC genes can be ligated to a vector that functions in the host bacterium, for example, a multi-copy vector, to thereby prepare a recombinant DNA, and the recombinant DNA is used to transform the host bacterium.

When using the gadA, gadB and gadC genes of *Escherichia coli*, the gadA, gadB and gadC genes can be obtained by PCR (polymerase chain reaction; White, T. J. et al., Trends Genet. 5, 185 (1989)) using primers based on the nucleotide sequence of SEQ ID NOS: 1, 3 or 5, for example, primers of SEQ ID NOS: 8 and 9 (gadA gene), or 10 and 11 (gadBC operon), and a chromosomal DNA of *Escherichia coli* as the template. The gadA, gadB and gadC genes from another bacterium can also be obtained by PCR from the chromosomal DNA or genomic DNA library of the bacterium using, as primers, oligonucleotides prepared based on the known sequences of the gadA, gadB and gadC genes of the bacterium, or of the gadA, gadB and gadC genes of another kind of bacterium, or the known sequence of other glutamate dehydrogenase or glutamic acid/GABA antiporter; or hybridization using an oligonucleotide prepared based on the sequence as a probe. A chromosomal DNA can be prepared from a bacterium that serves as a DNA donor by the method of Saito and Miura (see H. Saito and K. Miura, Biochem. Biophys. Acta, 72, 619 (1963), Experiment Manual for Biotechnology, edited by The Society for Biotechnology, Japan, p 97-98, Baifukan Co., Ltd., 1992) or the like.

Then, a recombinant DNA can be prepared by ligating the gadA, gadB and gadC genes which have been amplified by PCR to a vector DNA which is capable of functioning in the host bacterium. Examples of the vector capable of functioning in the host bacterium can include vectors which are autonomously replicable in the host bacterium. Examples of a vector which is autonomously replicable in *Escherichia coli* can include pUC19, pUC18, pHSG299, pHSG399, pHSG398, pACYC184, (pHSG and pACYC are available from Takara Bio Inc.), RSF1010, pBR322, pMW219, pMW119 (pMW is available form Nippon Gene Co., Ltd.), and pSTV29 (Takara Bio Inc.).

To introduce a recombinant DNA prepared as described above into a microorganism, any known transformation method reported so far can be employed. For example, treating recipient cells with calcium chloride so as to increase the permeability of DNA, which has been reported for *Escherichia coli* (Mandel, M. and Higa, A., J. Mol. Biol., 53, 159 (1970)), and using competent cells prepared from growing cells to introduce a DNA, which has been reported for *Bacillus subtilis* (Duncan, C. H., Wilson, G. A. and Young, F. E., Gene, 1, 153 (1977)) can be employed. In addition to these methods, introducing a recombinant DNA into protoplast- or spheroplast-like recipient cells, which had been reported to be applicable to *Bacillus subtilis*, actinomycetes, and yeasts (Chang, S. and Choen, S. N., Molec. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Sci., USA, 75, 1929 (1978)), can be employed.

The copy number of the gadA, gadB and gadC genes can also be increased by introducing multiple copies of the genes into the chromosomal DNA of a bacterium. In this case, multiple copies of the gadA, gadB and gadC genes can be introduced into the chromosomal DNA in a separate procedure by using fragments or vectors containing each of the genes or in a single procedure by using a fragment or a vector containing all of the genes. Introduction of multiple copies of the genes into the chromosomal DNA of a bacterium can be attained by homologous recombination using a target sequence present on the chromosomal DNA in multiple copies. Such a sequence present on a chromosomal DNA in multiple copies can be a repetitive DNA or an inverted repeat present on the edge of a transposing element. The gadA, gadB and gadC genes can be integrated tandemly in a region adjacent to the chromosomal gadA, gadB and gadC genes, or integrated into a region redundantly which is not necessary for the function of the host bacterium. This gene integration can be performed with a temperature-sensitive plasmid or integration vector.

Alternatively, as disclosed in JP 2-109985 A, multiple copies of the gadA, gadB and gadC genes can be introduced into the chromosomal DNA by inserting the genes into a transposon, and transferring it so that multiple copies of the gene are integrated into the chromosomal DNA. Integration of these genes into the chromosome can be confirmed by Southern hybridization using a portion of the genes as a probe.

Furthermore, expression of the gadA, gadB and gadC genes can also be enhanced by, as described in WO 00/18935, substituting an expression regulatory sequence such as a promoter of the genes on a chromosomal DNA or of the genes on a plasmid with a stronger promoter, modifying the sequences of "-35 region" and "-10 region" so that the sequences become a consensus sequence, amplifying a regulator that increases expression of the genes, or deleting or attenuating a regulator that decreases expression of the genes. Examples of known strong promoters include lac promoter, trp promoter, trc promoter, tac promoter, araBA promoter, lambda phage PR promoter, PL promoter, tet promoter, T7 promoter, and Φ10 promoter. Meanwhile, a promoter or SD sequence of the gadA, gadB and gadC genes can be modified so as to become a more potent promoter and a more potent SD sequence. Examples of a method of evaluating the strength of a promoter and examples of strong promoters are described in Goldstein et al. (Prokaryotic promoters in biotechnology. Biotechnol. Annu. Rev., 1995, 1, 105-128) or the like. In addition, it is known that a spacer sequence between the ribosome binding site (RBS) and translation initiation codon, especially, several nucleotides just upstream of the initiation codon, has a great influence on translation efficiency. Therefore, this sequence can be modified. Expression regulatory sequences of the gadA, gadB and gadC genes can be identified using a vector for promoter identification or genetic analysis software such as GENETYX. By substituting or modifying an expression regulatory sequence such as a promoter as described above, expression of the gadA, gadB and gadC genes can be enhanced. Substitution of the expression regulatory sequence can also be performed by using a temperature sensitive plasmid or by Red-driven integration (WO2005/010175).

An example of the regulator that increases expression of the gadA, gadB, and gadC genes can include GadX (SEQ ID NO: 22), while an example of the regulator that decreases expression of the gadA, gadB, and gadC genes can include GadW (SEQ ID NO: 24) (Ma, Z., Richard, H., Tucker, D. L., Conway, T., Foster, J. W. Collaborative regulation of *Escherichia coli* glutamate-dependent acid resistance by two AraC-like regulators, GadX and GadW (YhiW), J. Bacteriol. 184: 7001-7012. 2002). Therefore, the glutamate decarboxylase activity can also be improved by amplifying gadx gene (e.g., a gene encoding amino acid sequence at least 95% homologous to SEQ ID NO: 23) or disrupting gadw gene (e.g., a gene encoding amino acid sequence at least 95% homologous to SEQ ID NO: 25).

<2> Method of Producing L-Amino Acid

The method of producing an L-amino acid in accordance with the presently disclosed subject matter can include cultivating the bacterium of the present invention as described above in a medium to produce and cause accumulation of an L-amino acid in the medium or bacterial cells, and collecting the L-amino acid from the medium or the bacterial cells.

A conventional medium to be used for fermentative production of an L-amino acid using a bacterium can be used. That is, a general medium containing a carbon source, nitrogen source, inorganic ion, and if necessary, other organic components can be used. In accordance with the presently disclosed subject matter, examples of the carbon source can include sugars such as glucose, sucrose, lactose, galactose, fructose and a starch hydrolysate; alcohols such as glycerol and sorbitol; and organic acids such as fumaric acid, citric acid and succinic acid. Examples of the nitrogen source include inorganic ammonium salts such as ammonium sulfate, ammonium chloride and ammonium phosphate; an organic nitrogen such as a soybean hydrolysate; ammonia gas; and aqueous ammonia. As organic trace nutrients, auxotrophic substances such as vitamin B1 and L-homoserine, yeast extract, and the like can be contained in the medium in an appropriate amount. Besides such substances, if necessary, potassium phosphate, magnesium sulfate, iron ion, manganese ion, or the like can be added in small amounts. The medium to be used in accordance with the presently disclosed subject matter can be a natural medium or a synthetic medium as long as it contains a carbon source, nitrogen source, inorganic ion, and if necessary, other organic trace nutrients.

L-amino acids which improve the growth or productivity can be added. For example, L-threonine, L-homoserine, or L-isoleucine can be added in L-lysine fermentation, and L-isoleucine, L-lysine, L-glutamic acid, or L-homoserine can be added in L-threonine fermentation, and L-phenylalanine, or L-tyrosine can be added in L-tryptophan fermentation. These amino acids are usually added at a concentration of 0.01-10 g/L.

Trehalose can be added to the culture medium. Trehalose can be added to the medium at a concentration of at least 0.1 g/L in one example, at a concentration of at least 0.2 g/L in another example, and at a concentration of at least 0.5 g/L in another example. Crystallized trehalose can be solubilized and added to the medium, or trehalose present in the fermentation mother liquor which is obtainable after isolating target substances from fermentation solution can be added to the medium. Trehalose can be present in the medium as a by-product of fermentation.

Furthermore, betaine such as N-methylglycine, N,N-dimethylglycine, N,N,N-trimethylglycine and [2-hydroxyethyl] trimethylammonium can be added to the medium together with trehalose to improve productivity of the target substance. Betaine can be added to the medium preferably at a concentration of at least 0.1 g/L in one example, at a concentration of at least 0.25 g/L in another example, and at a concentration of at least 0.5 g/L in another example.

The culture, in one example, can be performed under aerobic conditions for 1 to 7 days at a temperature of 24° C. to 37° C. and a pH of 5 to 9. The pH can be adjusted with an inorganic or organic acidic or alkaline substance, ammonia gas or the like. The L-amino acid can be collected from the fermentation liquid by a conventional method such as ion-exchange resin, precipitation, and other known methods. When the L-amino acid accumulates in the bacterial cells, the L-amino acid can be collected, for example, by disrupting the bacterial cells by ultrasonication or the like to release L-amino acid into the supernatant fraction, and then the bacterial cells can be removed by centrifugation, followed by subjecting the resulting supernatant to an ion-exchange resin or the like.

When producing a basic amino acid, fermentation can be performed while controlling the pH of the medium during culture to 6.5-9.0 and controlling the pH of the medium after completion of the culture to 7.2-9.0, as well as controlling the pressure in the fermentation tank during fermentation so that it is positive. Alternatively, carbon dioxide or a mixed gas containing carbon dioxide can be added to the medium so that a bicarbonate ion and/or carbonate ion are present in an amount of at least 2 g/L in the culture medium during the culture period. These ions then function as counter ions against the cation of the basic amino acids, and the target basic amino acid may be collected (JP 2002-065287 A and US 2002025564).

EXAMPLES

Hereinafter, the presently disclosed subject matter will be described in more detail by referring to examples.

Example 1

<Construction of a Plasmid For Amplifying gadA and gadBC Operon>
<1-1> Construction of a Plasmid For Gene Amplification The entire nucleotide sequences of the genomes of *Escherichia coli* (*Escherichia coli* K-12 strain) (Genbank Accession No. U00096) have been reported (Science, 277, 1453-1474 (1997)). A plasmid pMWPthr was used for gene amplification. The plasmid has a promoter sequence (SEQ ID NO: 7) of the threonine operon (thrABC) from *Escherichia coli* chromosome between HindIII site and XbaI site of a vector pMW118 (manufactured by Nippon Gene Co., Ltd.) and can amplify a gene by inserting the gene downstream of the promoter.

<1-2> Construction of a Plasmid For Amplifying gadA Gene

Based on the nucleotide sequence of a gadA gene from *Escherichia coli* chromosome (sequence complementary to 3664203 . . . 3665603 of GenBank Accession No. U00096), PCR was performed using a synthetic oligonucleotide of SEQ ID NO: 8 having a SmaI site as a 5'-primer and a synthetic oligonucleotide of SEQ ID NO: 9 having a SacI site as a 3'-primer and using the genomic DNA of *Escherichia coli* W3110 strain as a template, followed by treatment with restriction enzymes SmaI and SacI, to thereby yield a gene fragment containing the gadA gene. The purified PCR product was ligated to the vector pMWPthr which had been digested with SmaI and SacI to construct a plasmid of pMWgadA for amplifying gadA.

<1-3> Construction of a Plasmid For Amplifying gadBC

Based on the nucleotide sequence of an gadBC operon from *Escherichia coli* chromosome (sequence complementary to 1566978 . . . 1570069 of GenBank Accession No. U00096), PCR was performed using a synthetic oligonucleotide of SEQ ID NO: 10 having a SmaI site as a 5'-primer and a synthetic oligonucleotide of SEQ ID NO: 11 having a SacI site as a 3'-primer and using the genomic DNA of *Escherichia coli* W3110 strain as a template, followed by treatment with restriction enzymes SmaI and SacI, to thereby yield a gene fragment containing the gadBC operon. The purified PCR product was ligated to a vector pMWPthr digested with SmaI and SacI to construct a plasmid of pMWgadBC for amplifying gadBC.

Example 2

<2-1> Construction of a Strain in Which the Lysine Decarboxylase-Encoding Genes (cadA and ldcC) Are Disrupted A strain which produces no lysine decarboxylase was constructed. The lysine decarboxylases are encoded by the cadA gene (GenBank Accession No. NP_418555, SEQ ID NO: 12) and the ldcC gene (Genbank Accession No. NP_414728, SEQ ID NO: 14) (WO 96/17930). *Escherichia coli* L-lysine producing WC196 strain which is resistant to AEC (S-(2-aminoethyl)-L-cysteine) was used as a parent strain (WO 96/17930).

Disruption of the cadA gene and the ldcC gene was performed by the method developed by Datsenko and Wanner, which is called "Red-driven integration" (Proc. Natl. Acad. Sci. USA, 2000, vol. 97, No. 12, p 6640-6645) and by an excision system derived from λ phage (J. Bacteriol. 2002 September; 184(18): 5200-3. Interactions between integrase and excisionase in the phage lambda excisive nucleoprotein complex. Cho E H, Gumport R I, Gardner J F.). "Red-driven integration" makes it possible to construct a gene-disrupted strain in one step by employing a PCR product obtained by using as primers synthetic oligonucleotides designed to have a part of the targeted gene on the 5'-ends and a part of an antibiotic-resistance gene on the 3'-ends. Combining the λ phage-derived excision system permits the removal of the antibiotic-resistance gene that has been incorporated into the gene-disrupted strain (JP2005-058227).

<2-2> Disruption of the cadA Gene

The plasmid pMW118-attL-Cm-attR (JP2005-058227) was used as a template for PCR. The plasmid pMW118-attL-Cm-attR was obtained by inserting the attL gene and attR gene, which are attachment sites of λ phage, and the cat gene, which is an antibiotic resistance gene, into pMW118 (Takara Bio Inc.) The genes are arranged in the following order: attL-cat-attR.

PCR was performed using, as primers, the synthetic oligonucleotides of SEQ ID NOS: 16 and 17, which have sequences corresponding to attL and attR on the 3'-terminals and a sequence corresponding to a part of the targeted cadA gene on the 5'-terminals.

The amplified PCR product was purified on an agarose gel and introduced into *Escherichia coli* WC196 strain by electroporation. This strain contains the plasmid pKD46 which has temperature-sensitive replicability. The plasmid pKD46 (Proc. Natl. Acad. Sci. USA, 2000, vol. 97, No. 12, p 6640-6645) contains a DNA fragment of 2,154 nucleotides derived from λ phage which contains the Red recombinase-encoding genes (γ, β, and exo genes) of the λ Red homologous recombination system which is controlled by an arabinose-inducible ParaB promoter (GenBank/EMBL Accession No. J02459, nucleotide numbers 31088 to 33241). The plasmid pKD46 is necessary to integrate the PCR product into the chromosome of the WC196 strain.

Competent cells for electroporation were prepared as follows. That is, cells of the *Escherichia coli* WC196 strain were cultured overnight at 30° C. in LB medium containing 100 mg/L ampicillin, and then diluted 100-fold with 5 mL of SOB medium (Sambrook, J., and Russell, D. W., Molecular Cloning: A Laboratory Manual/Third Edition. New York: Cold Spring Harbor Laboratory Press (2001)) containing ampicillin (20 mg/L) and L-arabinose (1 mM). The diluted cells were grown with aeration at 30° C. until OD600 reached about 0.6, and then concentrated 100-fold and washed three times with 10% glycerol so that the cells were available for electroporation. The electroporation was performed with 70 μL of the competent cells and about 100 ng of the PCR product. After the electroporation, 1 mL of SOC medium (Molecular Cloning: Laboratory manual, 2nd edition, Sambrook, J. et al., Cold Spring Harbor Laboratory Press (1989)) was added to the cells, cells were cultured at 37° C. for 2.5 hours, and then subjected to plate culture onto L-agar medium containing Cm (chloramphenicol) (25 mg/L), to thereby select Cm-resistant recombinant strains. Subsequently, to remove the plasmid pKD46, the cells were subcultured twice at 42° C. on L-agar medium containing Cm, and ampicillin resistance of the resultant colonies were examined, to thereby yield ampicillin-sensitive strains in which pKD46 was removed.

Deletion of the cadA gene in the mutant strain, which had been identified by the chloramphenicol resistance gene, was confirmed by PCR. The cadA-disrupted strain was named WC196ΔcadA::att-cat strain.

Subsequently, the above-mentioned helper plasmid pMW-intxis-ts (JP 2005-058827 A) was used to remove the att-cat gene which had been introduced into the cadA gene. The plasmid pMW-intxis-ts carries the gene encoding integrase (Int) of λ phage, and the gene encoding excisionase (Xis), and has temperature-sensitive replicability.

Competent cells of the WC196ΔcadA::att-cat strain were prepared by a conventional method, and were then transformed with the helper plasmid pMW-intxis-ts. These cells were then subjected to plate culture at 30° C. onto L-agar medium containing 50 mg/L ampicillin, to thereby select ampicillin-resistant strains.

Subsequently, to remove the plasmid pMW-intxis-ts, the cells were subcultured twice at 42° C. on L-agar medium. Then, ampicillin resistance and chloramphenicol resistance of the resulting colonies were examined, to thereby yield a chloramphenicol and ampicillin-sensitive strain, in which the cadA gene was disrupted, and att-cat and pMW-intxis-ts were removed. The strain was named WC196ΔcadA.

<2-3> Disruption of the ldcC Gene in the WC196ΔcadA Strain

Disruption of the ldcC gene in the WC196ΔcadA strain was performed by using oligonucleotides of SEQ ID NOS: 18 and 19 as primers in the same way as described above. Thereby, a cadA and ldcC-disrupted strain, WC196ΔcadAΔldcC was obtained.

Example 3

Effects of Amplification of gadA and gadBC in L-Lysine-Producing Strain of *Escherichia* Bacterium <3-1> Introduction of the Plasmid for Lysine Production Into WC196ΔcadAΔldcC Strain WC196ΔcadAΔldcC strain was transformed with a plasmid for lysine production, pCAB1 (WO 01/53459), which carries dapA, dapB, and lysC genes, by a conventional method, to thereby yield WC196ΔcadAΔldcC/pCAB1 strain (WC196LC/pCAB1).

Then, WC196LC/pCAB1 strain was transformed with the plasmids prepared in Example 1: the plasmid for amplifying gadA, pMWgadA; and the plasmid for amplifying gadBC, pMWgadBC, respectively, to thereby yield ampicillin-resistant strains. Introduction of the plasmids was confirmed, and the strain introduced with the plasmid for amplifying gadA (pMWgadA) and the strain introduced with the plasmid for amplifying gadBC (pMWgadBC) were named WC196LC/pCAB1/gadA strain and WC196LC/pCAB1/gadBC strain, respectively. Meanwhile, a strain transformed with pMW118 was obtained as a control, and named WC196LC/pCAB1/pMW118.

The strains prepared above were cultured at 37° C. in an LB medium containing 25 mg/L streptmycin and 50 mg/L ampicillin until the OD600 reached about 0.6, and then a 40% glycerol solution was added in the same amount as that of the culture, followed by stirring. Then, the solution was dispensed in appropriate amounts and stored in glycerol at −80° C.

<3-2> Culture for Lysine Production

The glycerol stocks of the strains were thawed, and 100 μL of each of the glycerol stocks was uniformly applied on an L-plate containing 50 mg/L ampicillin, and the culture was performed at 37° C. for 24 hours. About one-eighth of the bacterial cells on the plate were inoculated into 20 mL of the fermentation medium described below containing 50 mg/L ampicillin in a 500-mL Sakaguchi flask, and culture was performed at 37° C. for 48 hours with a reciprocal shaker. After the culture, the amount of L-lysine accumulated in the medium was determined using Biotech analyzer AS210 (manufactured by Sakura Finetek Japan Co., Ltd.). The composition of the medium used in the culture is shown below.

| [L-lysine production medium for *Escherichia* bacteria] | |
|---|---|
| Glucose | 40 g/L |
| (NH$_4$)$_2$SO$_4$ | 16 g/L |
| KH$_2$PO$_4$ | 1.0 g/L |
| MgSO$_4$•7H$_2$O | 1.0 g/L |
| FeSO$_4$•7H$_2$O | 0.01 g/L |
| MnSO$_4$•7H$_2$O | 0.01 g/L |
| Yeast extract | 2.0 g/L |
| CaCO$_3$ (official grade) | 30 g/L |

The medium was adjusted to pH 7.0 with KOH and sterilized using an autoclave at 120° C. for 20 minutes. Glucose and MgSO$_4$.7H$_2$O were mixed and separately sterilized. CaCO$_3$ was added after dry heat sterilization.

Table 1 shows the OD and amounts of L-lysine accumulated after 48 hours.

TABLE 1

Effects of amplification of gadA and gadBC in L-lysine producing bacterium WC196LC/pCAB1

| Strain name | OD (600 nm) | Concentration of Lys(g/l) |
|---|---|---|
| WC196LC/pCAB1/pMW118 | 7.8 | 14.3 |
| WC196LC/pCAB1/gadA | 7.6 | 15.0 |
| WC196LC/pCAB1/gadBC | 7.5 | 15.3 |

In the cases of the strain in which gadA gene was amplified (WC196LC/pCAB1/gadA) and the strain in which gadBC operon was amplified (WC196LC/pCAB1/gadBC), the amounts of L-lysine which accumulated were significantly high as compared to the control (WC196LC/pCAB1/pMW118).

Example 4

Effects of Amplification of gadA and gadBC in L-threonine Producing Strain of *Escherichia* Bacterium

*Escherichia coli* B-5318 strain (see EP 0593792) was used as an L-threonine producing strain of *Escherichia coli*.

The B-5318 strain was transformed with the plasmid pMWgadBC prepared in Example 1 for amplifying gadBC to select an ampicillin-resistant strain. Introduction of the plasmid was confirmed, and the strain introduced with the plasmid pMWgadBC for amplifying gadBC was named B-5318/gadBC strain. B-5318/pMW118 strain obtained by introducing pMW118 was used as a control.

The strains prepared above were cultured at 37° C. in an LB medium containing 50 mg/L ampicillin until the OD600 reached about 0.6, and then a 40% glycerol solution was added in the same amount as that of the culture, followed by stirring. Then, the solution was dispensed in appropriate amounts and stored in glycerol at −80° C.

The glycerol stocks of the strains were thawed, and 100 μL of each of the glycerol stocks was uniformly applied on an L-plate containing 50 mg/L ampicillin, and culture was performed at 37° C. for 24 hours. About one-eighth of the bacterial cells on the plate were inoculated into 20 mL of the fermentation medium described below containing 50 mg/L ampicillin in a 500-mL Sakaguchi flask, and culture was performed at 40° C. for 18 hours with a reciprocal shaker. After the culture, the amounts of L-threonine which accumulated in the medium were determined using an amino acid analyzer L-8500 (manufactured by Hitachi, Ltd.). The composition of the medium used in the culture is shown below.

[L-threonine production medium for *Escherichia* bacteria]

| | |
|---|---|
| Glucose | 40 g/L |
| $(NH_4)_2SO_4$ | 16 g/L |
| $KH_2PO_4$ | 1.0 g/L |
| $MgSO_4 \cdot 7H_2O$ | 1.0 g/L |
| $FeSO_4 \cdot 7H_2O$ | 0.01 g/L |
| $MnSO_4 \cdot 7H_2O$ | 0.01 g/L |
| Yeast extract | 2.0 g/L |
| $CaCO_3$ (official grade) | 30 g/L |

The medium was adjusted to pH 7.0 with KOH and sterilized using an autoclave at 120° C. for 20 minutes. Glucose and $MgSO_4 \cdot 7H_2O$ were mixed and separately sterilized. $CaCO_3$ was added after dry heat sterilization.

Table 2 shows the OD and amounts of L-threonine accumulated after 18 hours.

TABLE 2

Effect of amplification of gadBC operon in L-threonine producing strain B-5318

| Strain name | OD (600 nm) | Concentration of Thr (g/l) |
|---|---|---|
| B-5318/pMW118 | 9.2 | 7.3 |
| B-5318/gadBC | 9.5 | 7.6 |

In the case of the strain in which gadBC operon was amplified (B-5318/gadBC), growth and the amounts of L-threonine which accumulated were significantly higher as compared to the control (B-5318). Therefore, the results suggested that simultaneous enhancement of glutamate decarboxylase and glutamic acid/GABA antiporter was also effective for improving L-threonine productivity.

[Explanation of the Sequence Listing]

SEQ ID NO: 1: nucleotide sequence of the gadA gene
SEQ ID NO: 2: amino acid sequence encoded by the gadA gene
SEQ ID NO: 3: nucleotide sequence of the gadB gene
SEQ ID NO: 4: amino acid sequence encoded by the gadB gene
SEQ ID NO: 5: nucleotide sequence of the gadC gene
SEQ ID NO: 6: amino acid sequence encoded by the gadC gene
SEQ ID NO: 7: nucleotide sequence of threonine operon promoter
SEQ ID NO: 8: 5'-primer for amplifying the gadA gene
SEQ ID NO: 9: 3'-primer for amplifying the gadA gene
SEQ ID NO: 10: 5'-primer for amplifying the gadBC operon
SEQ ID NO: 11: 3'-primer for amplifying the gadBC operon
SEQ ID NO: 12: nucleotide sequence of the cadA gene
SEQ ID NO: 13: amino acid sequence encoded by the cadA gene
SEQ ID NO: 14: nucleotide sequence of the ldcC gene
SEQ ID NO: 15: amino acid sequence encoded by the ldcC gene
SEQ ID NO: 16: primer for disrupting the cadA gene
SEQ ID NO: 17: primer for disrupting the cadA gene
SEQ ID NO: 18: primer for disrupting the ldcC gene
SEQ ID NO: 19: primer for disrupting the ldcC gene
SEQ ID NO: 20: primer for amplifying the gadB gene
SEQ ID NO: 21: primer for amplifying the gadC gene
SEQ ID NO: 22: nucleotide sequence of the gadX gene
SEQ ID NO: 23: amino acid sequence encoded by the gadX gene
SEQ ID NO: 24: nucleotide sequence of the gadW gene
SEQ ID NO: 25: amino acid sequence encoded by the gadW gene

INDUSTRIAL APPLICABILITY

According to the method of the present invention, L-lysine, L-threonine and L-tryptophan can be efficiently produced by fermentation.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

What is claimed is:

1. A method for producing an L-amino acid selected from the group consisting of L-lysine and L-threonine, the method comprising cultivating an L-amino acid producing *E. coli* bacterium in a medium; and collecting the L-amino acid from the medium, wherein the L-amino acid producing *E. coli* bacterium is modified to enhance glutamate decarboxylase activity by a method selected from the group consisting of:
- A) transformation of the *E. coli* bacterium with a multi-copy vector comprising a gene selected from the group consisting of gadA and gadB,
- B) increasing the copy number of a gene selected from the group consisting of gadA and gadB by introduction of the gene into the chromosome of the *E. coli* bacterium,
- C) replacing a promoter for a gene selected from the group consisting of gadA and gadB with a stronger promoter, and
- D) combinations thereof;

wherein the gadA gene is a DNA selected from the group consisting of:
- (a) a DNA comprising the nucleotide sequence of SEQ ID NO: 1; and
- (b) a DNA that hybridizes with the entire nucleotide sequence complementary to SEQ ID NO: 1 under stringent conditions comprising washing at 68° C. in a salt concentration of 0.1×SSC and 0.1% SDS, and wherein said DNA encodes a protein that has glutamate decarboxylase activity, wherein the gadB gene is a DNA selected from the group consisting of:
- (c) a DNA comprising the nucleotide sequence of SEQ ID NO: 3; and
- (d) a DNA that hybridizes with the entire nucleotide sequence complementary to SEQ ID NO: 3 under stringent conditions comprising washing at 68° C. in a salt concentration of 0.1×SSC and 0.1% SDS, and wherein said DNA encodes a protein that has glutamate decarboxylase activity.

2. The method according to claim 1, wherein the gadA gene encodes a protein selected from the group consisting of: (A) a protein comprising the amino acid sequence of SEQ ID NO: 2; and (B) a protein comprising a polypeptide having not less than 95% homology to the amino acid sequence of SEQ ID NO: 2, wherein the polypeptide has glutamate decarboxylase activity.

* * * * *